US009943660B2

(12) United States Patent
Selvarajan et al.

(10) Patent No.: US 9,943,660 B2
(45) Date of Patent: Apr. 17, 2018

(54) NASAL PRONGS FOR MASK SYSTEM

(75) Inventors: Karthikeyan Selvarajan, Thornleigh (AU); David Rae Gale, Wahroonga (AU); Robin Garth Hitchcock, Carlingford (AU); Muditha Pradeep Dantanarayana, Cherrybrook (AU)

(73) Assignee: RESMED LIMITED, Bella Vista (AU)

( * ) Notice: Subject to any disclaimer, the term of this patent is extended or adjusted under 35 U.S.C. 154(b) by 1012 days.

(21) Appl. No.: 12/309,917

(22) PCT Filed: Jul. 30, 2007

(86) PCT No.: PCT/AU2007/001060
§ 371 (c)(1),
(2), (4) Date: Feb. 3, 2009

(87) PCT Pub. No.: WO2008/014543
PCT Pub. Date: Feb. 7, 2008

(65) Prior Publication Data
US 2009/0320851 A1 Dec. 31, 2009

Related U.S. Application Data

(60) Provisional application No. 60/852,649, filed on Oct. 19, 2006, provisional application No. 60/835,442, filed on Aug. 4, 2006.

(51) Int. Cl.
*A61M 16/00* (2006.01)
*A61M 16/06* (2006.01)
(52) U.S. Cl.
CPC .... *A61M 16/0666* (2013.01); *A61M 16/0683* (2013.01)

(58) Field of Classification Search
CPC .......... A61M 16/06; A61M 2210/0618; A61M 16/0683; A61M 2016/0616;
(Continued)

(56) References Cited

U.S. PATENT DOCUMENTS 2,535,155 A * 12/1950 Pandorf ................... 128/204.12
2,604,094 A * 7/1952 Miller et al. ............. 128/203.15
(Continued)

FOREIGN PATENT DOCUMENTS

WO WO 1987/003704 6/1987
WO WO 99/58181 A1 11/1999
(Continued)

OTHER PUBLICATIONS

Extended European Search Report issued in a corresponding European Application No. 07784705.1 dated Dec. 5, 2013.
(Continued)

*Primary Examiner* — (Jackie) Tan-Uyen T Ho
*Assistant Examiner* — Ned T Heffner
(74) *Attorney, Agent, or Firm* — Nixon & Vanderhye, P.C.

(57) ABSTRACT

A nasal prong for sealing with a nasal passage of a patient includes a head portion structured to seal and/or sealingly communicate with the patient's nasal passage and a column or stalk structured to interconnect the head portion with a base. The nasal prong is structured to redirect air flow direction, diffuse air flow or create turbulence, and/or orient a prong orifice in order to reduce and/or eliminate air jetting effects.

49 Claims, 22 Drawing Sheets

(58) Field of Classification Search
CPC .............. A61M 16/0666; A61M 15/08; A61M 15/085; A61M 16/0688; A61M 16/0866; A61M 16/106; A61M 16/208; A61M 29/00; A61M 16/00; A61M 16/0616; A61F 5/08; A61F 5/56; A61B 17/24; A61B 2017/248; A61B 5/085; A62B 23/06; A62B 7/10; A62B 9/06
USPC ............ 128/206.26, 206.28, 207.13, 203.22, 128/206.11, 207.18, 200.24, 200.26, 128/202.27, 848; 600/533; 606/198
See application file for complete search history.

(56) References Cited

U.S. PATENT DOCUMENTS

| | | | |
|---|---|---|---|
| 3,400,714 A | | 9/1968 | Sheridan |
| 3,905,335 A | * | 9/1975 | Kapp ........................ 128/206.11 |
| 4,052,983 A | * | 10/1977 | Bovender ................. 128/204.12 |
| 4,782,832 A | * | 11/1988 | Trimble et al. ........... 128/207.18 |
| 4,907,583 A | * | 3/1990 | Wetterlin ............... A61M 15/00 128/200.18 |
| 4,907,584 A | * | 3/1990 | McGinnis ............... A61M 16/06 128/206.24 |
| 5,099,836 A | * | 3/1992 | Rowland et al. ......... 128/204.23 |
| 5,724,965 A | | 3/1998 | Handke |
| 6,342,040 B1 | * | 1/2002 | Starr et al. .................... 600/538 |
| 6,439,230 B1 | * | 8/2002 | Gunaratnam et al. ... 128/206.21 |
| 6,561,188 B1 | | 5/2003 | Ellis |
| 6,986,351 B2 | | 1/2006 | Figley et al. |
| 7,080,645 B2 | | 7/2006 | Genger et al. |
| D533,269 S | * | 12/2006 | McAuley et al. ......... D24/110.6 |
| 7,318,437 B2 | | 1/2008 | Gunaratnam et al. |
| 2003/0094178 A1 | * | 5/2003 | McAuley et al. ........ 128/207.18 |
| 2005/0028822 A1 | * | 2/2005 | Sleeper et al. .......... 128/207.18 |
| 2005/0039757 A1 | | 2/2005 | Wood |
| 2005/0051177 A1 | | 3/2005 | Wood et al. |
| 2005/0103347 A1 | * | 5/2005 | Curti ................. A61M 16/0666 128/207.18 |
| 2005/0126574 A1 | | 6/2005 | Wood |
| 2005/0241644 A1 | | 11/2005 | Gunaratnam et al. |
| 2006/0107958 A1 | * | 5/2006 | Sleeper .................... 128/206.11 |
| 2006/0137690 A1 | | 6/2006 | Gunaratnam et al. |

FOREIGN PATENT DOCUMENTS

| | | | |
|---|---|---|---|
| WO | WO 2003/026559 | | 4/2003 |
| WO | WO03026559 A2 | * | 4/2003 |
| WO | WO 03026559 A2 | * | 4/2003 |
| WO | WO 2004/073778 A1 | | 9/2004 |
| WO | PCT/AU2004/001832 | | 12/2004 |
| WO | WO 2005/016407 | | 2/2005 |
| WO | WO 2005063328 A1 | * | 7/2005 |
| WO | WO 2005/079726 | | 9/2005 |
| WO | WO 2006/024253 A1 | | 3/2006 |
| WO | WO 2006/130903 | | 12/2006 |
| WO | PCT/AU2007/000770 | | 5/2007 |
| WO | WO 2007/053878 | | 5/2007 |

OTHER PUBLICATIONS

Communication Pursuant to Article 94(3) EPC dated Apr. 12, 2017 in European Application No. 07784705.1 (10 pages).

* cited by examiner

FRONT

SIDE

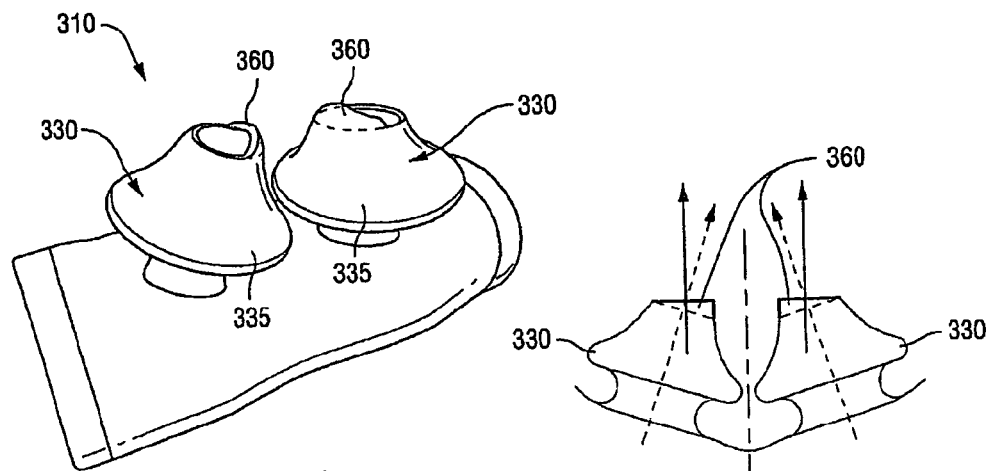
FIG. 4-1
FIG. 4-2
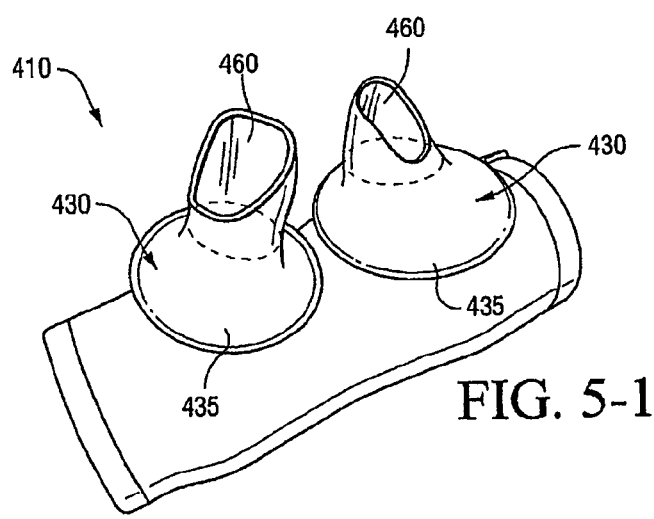
FIG. 5-1
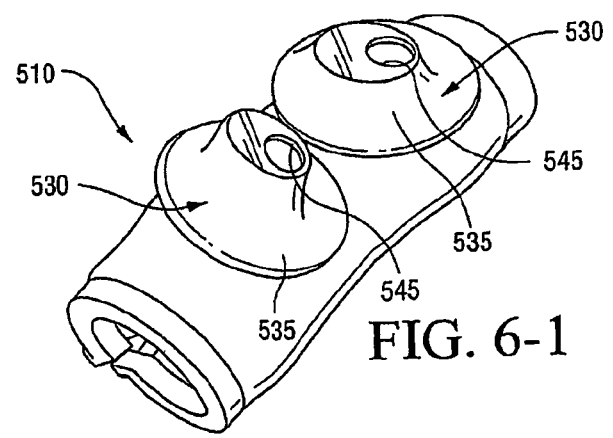
FIG. 6-1

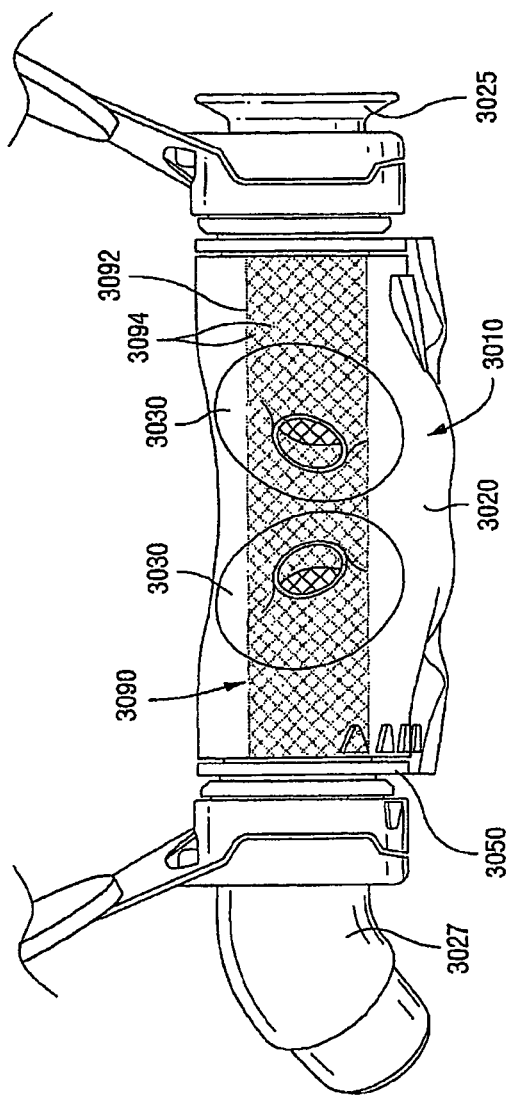
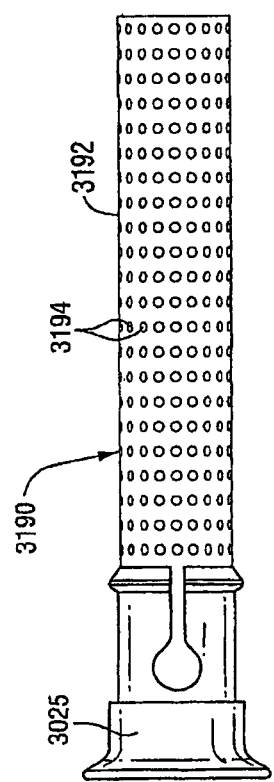
FIG. 28-3
FIG. 28-4

NASAL PRONGS FOR MASK SYSTEM

CROSS-REFERENCE TO APPLICATION

This application is the U.S. national phase of International Application No. PCT/AU2007/001060, filed Jul. 30, 2007, which designated the U.S. and claims the benefit of U.S. Provisional Patent Application Nos. 60/835,442, filed Aug. 4, 2006, and 60/852,649, filed Oct. 19, 2006, each of which is incorporated herein by reference in its entirety.

FIELD OF THE INVENTION

The present invention relates to nasal prongs for a mask system for delivery of respiratory therapy to a patient. Examples of such therapies are Continuous Positive Airway Pressure (CPAP) treatment, Non-Invasive Positive Pressure Ventilation (NIPPV), and Variable Positive Airway Pressure (VPAP). The therapy is used for treatment of various respiratory conditions including Sleep Disordered Breathing (SDB) such as Obstructive Sleep Apnea (OSA).

BACKGROUND OF THE INVENTION

Nasal prongs (also referred to as nasal pillows, nozzles and cannulae) used in the treatment of SDB are designed for sealing inside and/or against respective nasal passages of the patient, such as against the outer, exposed surfaces of the nares. Air or other breathable gas is supplied by a blower and passed along a flexible conduit to the nasal prongs.

A common problem with known nasal prongs is patient comfort. For example, one common problem is irritation or discomfort of the inside of the patient's nostrils caused by air flow irritation (referred to as air jetting or jetting effect) when high velocity air, e.g., pressurized up to 14 cmH$_2$O or more, is passed through the nasal passages from the nasal prongs.

A known mask structured to minimize the sensation of air jetting is disclosed in U.S. Pat. No. 5,724,965, for example.

There is a continuous need in the art to provide nasal prongs with a high level of comfort by reducing and/or eliminating air jetting.

SUMMARY OF THE INVENTION

One aspect of the present invention relates to nasal prongs that provide more comfort to the patient.

Another aspect of the present invention relates to nasal prongs that structured to reduce and/or eliminate air jetting.

Another aspect of the present invention relates to a nasal prong for sealing with a nasal passage of a patient. The nasal prong includes a head portion structured to seal and/or sealingly communicate with the patient's nasal passage and a column or stalk structured to interconnect the head portion with a base. The head portion is configured to direct gas in use generally away from or along the septum and/or posteriorly relative to the nasal passage.

Another aspect of the present invention relates to a nasal prong for sealing with a nasal passage of a patient. The nasal prong is structured to create conditions for turbulence or dispersion within the nasal passage.

Another aspect of the present invention relates to a nasal prong for sealing with a nasal passage of a patient. The nasal prong is structured to redirect air flow direction, diffuse air flow or create turbulence, and/or orient the prong orifice in order to reduce and/or eliminate air jetting effects.

Another aspect of the present invention relates to a nasal prong for sealing with a nasal passage of a patient. The nasal prong includes a head portion structured to seal and/or sealingly communicate with the patients nasal passage and a column or stalk structured to interconnect the head portion with a base. The stalk is configured to direct air in a first direction and the head portion is configured to direct air in a second direction or vector that is angled with respect to the first direction.

Another aspect of the present invention relates to a nasal prong for sealing with a nasal passage of a patient. The nasal prong includes a head portion structured to seal and/or sealingly communicate with the patient's nasal passage and a column or stalk structured to interconnect the head portion with a base. The head portion is configured to provide sealing along a first plane and provide an exit orifice to direct gas along a vector or direction that is angled with respect to the first plane.

Another aspect of the present invention relates to a nasal prong for sealing with a nasal passage of a patient. The nasal prong includes a head portion structured to seal and/or sealingly communicate with the patient's nasal passage and a column or stalk structured to mount the head portion to a base. The head portion includes a hood, a rib, and/or a grate, each of which may include surface treatment.

Another aspect of the present invention relates to a nasal prong for sealing with a nasal passage of a patient. The nasal prong includes a head portion structured to seal and/or sealingly communicate with the patient's nasal passage and a column or stalk structured to mount the head portion to a base. The head portion includes an exit orifice that is offset from an axis of the stalk, has a triangular shape, and/or is angled with respect to a sealing plane.

Another aspect of the present invention relates to a nasal prong for sealing with a nasal passage of a patient. The nasal prong includes a head portion structured to seal and/or sealingly communicate with the patient's nasal passage and a column or stalk structured to mount the head portion to a base. The head portion has a dual-wall configuration including an inner wall and an outer wall that surrounds the inner wall. The inner wall and/or outer wall includes a hood, a rib, and/or a grate, each of which may include surface treatment.

Another aspect of the present invention relates to a nasal prong for sealing with a nasal passage of a patient. The nasal prong includes a head portion structured to seal and/or sealingly communicate with the patient's nasal passage and a column or stalk structured to mount the head portion to a base. The head portion has a dual-wall configuration including an inner wall and an outer wall that surrounds the inner wall. The inner wall includes one or more holes.

Another aspect of the present invention relates to a nasal prong for sealing with a nasal passage of a patient. The nasal prong includes a head portion structured to seal and/or sealingly communicate with the patient's nasal passage and a column or stalk structured to mount the head portion to a base. The head portion includes an anterior portion and a posterior portion. The anterior portion has a shape that is different than a shape of the posterior portion.

Another aspect of the present invention relates to a nasal prong for sealing with a nasal passage of a patient. The nasal prong includes a head portion structured to seal and/or sealingly communicate with the patient's nasal passage and a column or stalk structured to mount the head portion to a base. The head portion has a dual-wall configuration including an inner wall and an outer wall that surrounds the inner wall. An orifice of the inner wall and/or outer wall includes a series of contours or lobes.

Another aspect of the present invention relates to a mask system including a frame and a nasal prong assembly provided to the frame. The nasal prong assembly includes a base and a pair of nasal prongs provided to the base. A dispersion cartridge is adapted to extend through the base to create turbulence and/or disperse gas flow.

Another aspect of the present invention relates to a method for forming a dispersion cartridge adapted to create turbulence and/or disperse gas flow in a mask system. The method includes providing a flat piece of material that provides a plurality of openings or pores, rolling the material into cylindrical form, and inserting the cylinder into a frame, elbow, and/or end plug of the mask system to create turbulence and/or disperse gas flow.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-5 illustrate the nasal prong assembly isolated from the mask system shown in FIG. 1 and showing reference planes through the nasal prong assembly, FIGS. 2-3 to 2-5 also illustrating exemplary air flow ranges and angles according to an embodiment of the present invention;

FIG. 2-6 showing an exemplary human nose and an exemplary air flow direction according to an embodiment of the present invention; and FIGS. 3-1 to 3-3, 4-1 to 4-2, and 5-1 illustrate nasal prongs including hoods according to embodiments of the present invention;

FIGS. 6-1, 7-1, and 8-1 illustrate nasal prongs including shifted orifices according to embodiments of the present invention;

FIGS. 9-1, 9-2, and 10-1 illustrate nasal prongs including ribbing according to embodiments of the present invention;

FIGS. 11-1 to 11-2 and 12-1 to 12-2 illustrate nasal prongs including triangular orifices according to embodiments of the present invention;

FIGS. 13-1 to 13-2, 14-1, 15-1, 16-1 to 16-2, 17-1, and 18-1 to 18-2 illustrate nasal prongs including grates according to embodiments of the present invention;

FIGS. 19-1, 20-1, 21-1, 22-1 to 22-2, 23-1, 23-2 to 23-3, 24-1, and 25-1 illustrate nasal prongs including dual walls according to embodiments of the present invention;

FIGS. 26-1 to 26-2 illustrate a nasal prong including an angled orifice according to an embodiment of the present invention;

FIGS. 27-1 to 27-2 illustrate a nasal prong including a concave anterior portion according to an embodiment of the present invention;

FIGS. 28-1 to 28-3 illustrate various views of a disposable or re-useable dispersion catridge for a nasal prong assembly according to an embodiment of the present invention; and FIG. 28-4 illustrates a disposable or re-useable dispersion cartridge for a nasal prong assembly according to another embodiment of the present invention.

DETAILED DESCRIPTION OF ILLUSTRATED EMBODIMENTS

The following includes descriptions of several illustrated embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

Each illustrated embodiment includes features that may be used with the embodiments and/or components described in U.S. Non-Provisional application Ser. Nos. 10/781,929, 10/546,305, and 11/101,657, and PCT Appln. Nos. PCT/AU2004/001832 and PCT/AU2006/000770, as would be apparent to those of ordinary skill in the art. U.S. Non-Provisional application Ser. Nos. 10/781,929, 10/546,305, and 11/101,657 and PCT Appln. No. PCT/AU2006/000770 are each incorporated herein by reference in its entirety.

1. Known Nasal Prongs

Figure 1:
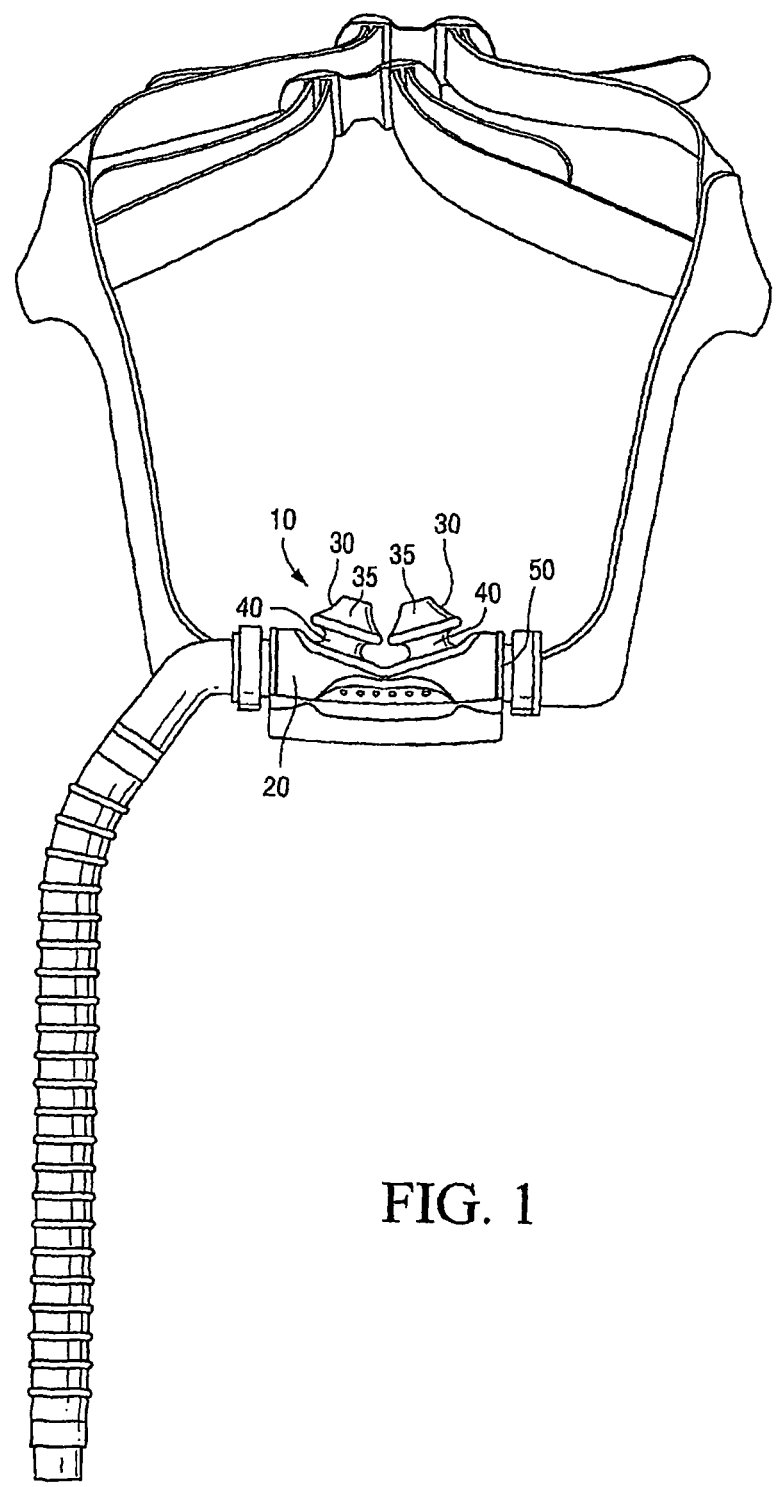
FIG. 1 is a perspective view of a mask system including a nasal prong assembly as known in the art.

FIG. 1 illustrates a mask system 5 including a nasal prong assembly 10 such as at that shown in the incorporated U.S. applications. As illustrated, the nasal prong assembly 10 includes a base 20 and a pair of nasal prongs 30 provided to the base 20. Each nasal prong 30 includes a head portion 35 adapted to seal and/or sealingly communicate with a respective patient nasal passage and a column or stalk 40 that interconnects the head portion 35 with the base 20. The nasal prong assembly 10 may be integrally formed in one-piece, e.g., by silicone in an injection molding process. The nasal prong assembly 10 is structured to be removably and replacably attached to a substantially rigid frame 50. One or more vent openings may be provided in the frame and/or base for $CO_2$ washout.

The known nasal prongs 30 are constructed and arranged to direct air into the patient's nasal passages in a predetermined flow direction or angle. FIGS. 2-1 to 2-5 illustrate four planes (i.e., plane A, plane B, plane C, and plane D) through the nasal prong assembly 10. Planes A, B, and C pass through respective ones of the three axes of a selected prong 30, and plane D passes through a vertical axis of the base 20.

Figures 1, 24:
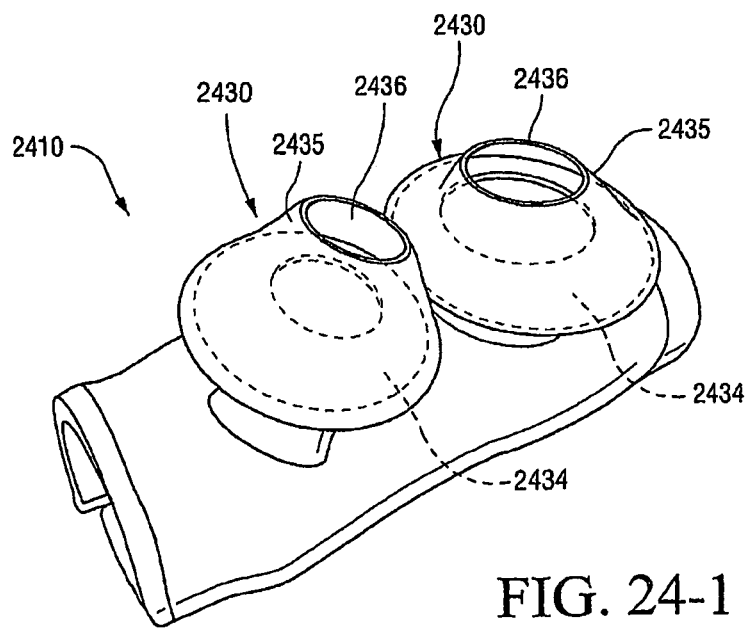

As illustrated, the nasal prongs 30 are mounted to the base 20 at an angle (e.g., plane B angled with respect to plane D as best shown in FIG. 24). In use, the prongs 30 "pinch" the nasal septum while directing air flow medially onto the septum (in the direction of plane B shown in FIG. 2-4) and superiorly into the nasal passage (in the direction of plane C shown in FIG. 2-5). The septum is the midline structure or wall inside the nose that divides the nose into left and right sides.

Such an air flow arrangement may be comfortable for a wide range of patients. For other patients, such an air flow arrangement may cause discomfort due to air jetting or directed flow onto the septum.

2. Nasal Prong Embodiments

The following embodiments describe alternative prong arrangements that are structured to improve comfort and fitting by reducing and/or eliminating the air jetting effect. Specifically, the following embodiments illustrate alternative prong arrangements structured to redirect air flow direction, diffuse air flow or create turbulence, and/or change the prong orifice in order to reduce and/or eliminate air jetting effects.

For example, a more comfortable prong may be structured to direct air flow superiorly rather than medially onto the septum (as viewed from the front). In an embodiment, air should be directed away from plane D and approach plane A to reduce the effect of air jetting and redirect the air away from close proximity tissue (i.e., the septum). Also, a more comfortable prong may be structured to direct air flow posteriorly into the nasal passage rather than superiorly straight up the nasal passage (as viewed from the side). In an embodiment, the orifice of the prong may be shifted more posteriorly and medially and directed superiorly.

FIGS. 2-3 to 2-5 show exemplary air flow ranges (shaded regions) and angles according to an embodiment of the present invention. In an embodiment, d1 may be about 3°, d2 may be about 40°, d3 may be about 5°, d4 may be about 35°, and d5 may be about 90°. As noted above, the shaded regions are selected to direct air away from the septum and towards the back of the patient's head. Although specific dimensions and ranges are shown in FIGS. 2-3 to 2-5, it is to be understood that these dimensions and ranges are merely exemplary and other dimensions and ranges are possible depending on application. For example, dimensions and ranges that vary from those provided +/−10% may be suitable for particular applications.

FIG. 2-6 illustrates an exemplary human nose and an exemplary air flow direction according to an embodiment of the present invention. As illustrated, air flow is preferably directed more posteriorly (arrow indicated in solid lines), e.g., towards the back of the patient's head, rather than straight up the nasal passage as in the old configuration (arrow indicated in dashed lines) to protect sensitive areas of the anterior nose. That is, the air flow indicated in dashed lines in FIG. 2-6 provides a jetting effect in which air is a directed flow at sensitive areas of the anatomy, which may cause cooling and/or drying in these sensitive areas. Accordingly, an aspect of the invention relates to nasal prongs that provide less directed flow and/or more turbulent flow. Turbulent flow provides flow with more energy so that it can travel around corners better. Also, an aspect of the invention relates to nasal prongs that provide increased dispersion, which may be done by turbulence. Dispersed air provides flow that is not directed at sensitive areas as much, e.g., air dispersed by creating small scale turbulence. Further, an aspect of the invention relates to nasal prongs that direct air away from sensitive areas of the patient's nose, e.g., such as air flow indicated in solid lines in FIG. 2-6.

In an alternative embodiment, the prongs may be configured to change (e.g., change continuously) air flow direction during therapy, e.g., to allow nasal mucosa to rest.

In yet another embodiment, the prongs may be configured to change air flow in concert with the nasal cycle, which is the normal cycle of congestion and decongestion of the nasal tissue to allow nasal mucosa to rest periodically. For example, independent flow in each nostril may be provided to address the nasal cycle. Such arrangements may increase the comfort of CPAP therapy.

Also, flow may be changed dependent on the patient's body position, e.g., side the patient is lying on. For example, the mask system may be configured to allow flow to be occluded in the inferior prong and open in the superior prong (if the patient is lying on his/her side), e.g., gravity flap, collapsible headgear tubing.

2.1 Hood to Direct Air

A hood may be provided to the head portion of the nasal prong to direct air flow. That is, the hood changes the air flow direction (with respect to the old configuration) to reduce and/or eliminate the air jetting effect, e.g., direct flow away from the septum.

In the illustrated embodiments, a hood is provided to an exterior portion of the prong. In alternative embodiments, a hood may be provided to an interior portion of the prong, e.g., at least partially within the head portion of the prong.

2.1.1 Anterior Hood

Figures 1, 2:
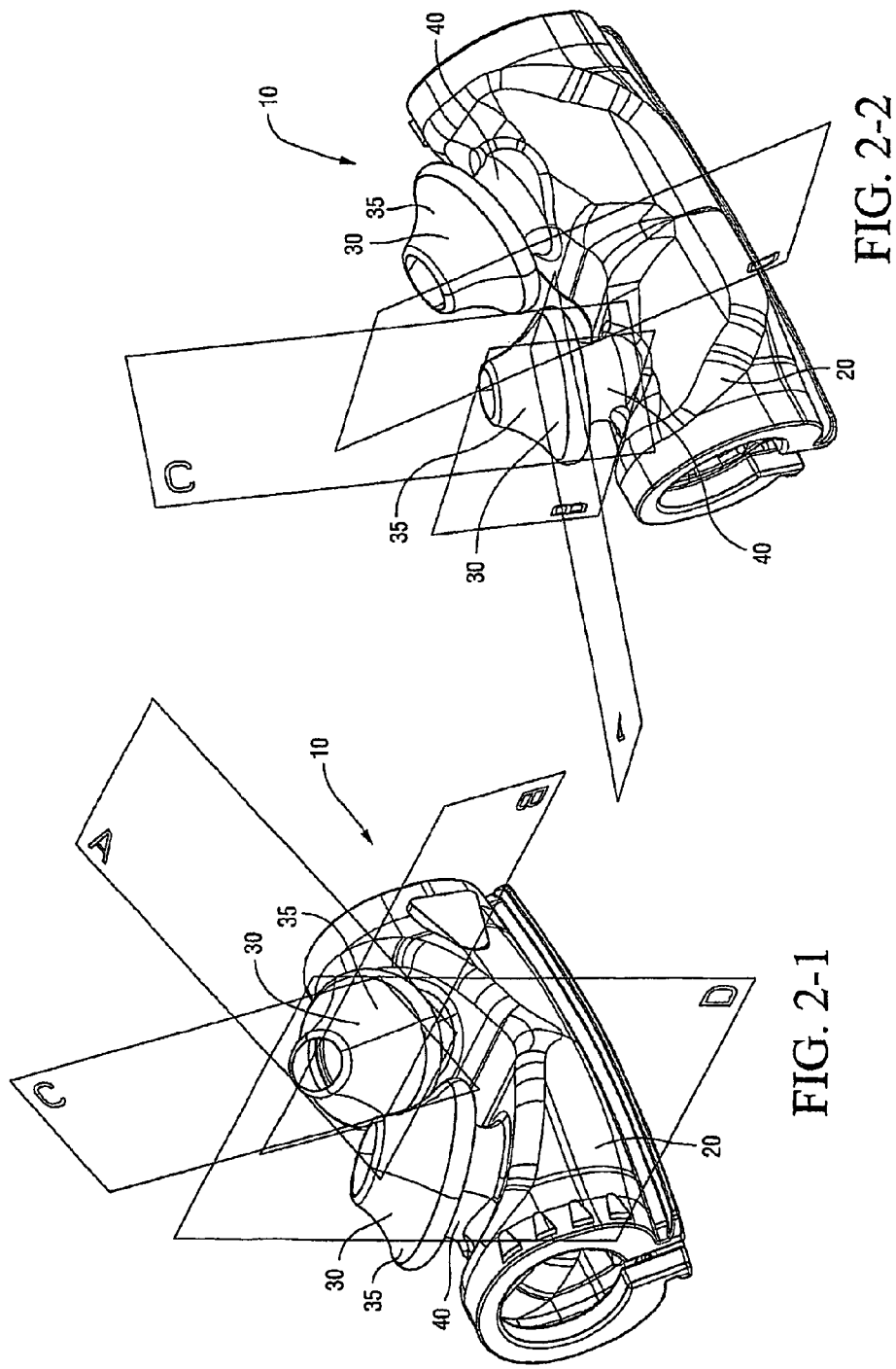
Figures 2, 3:
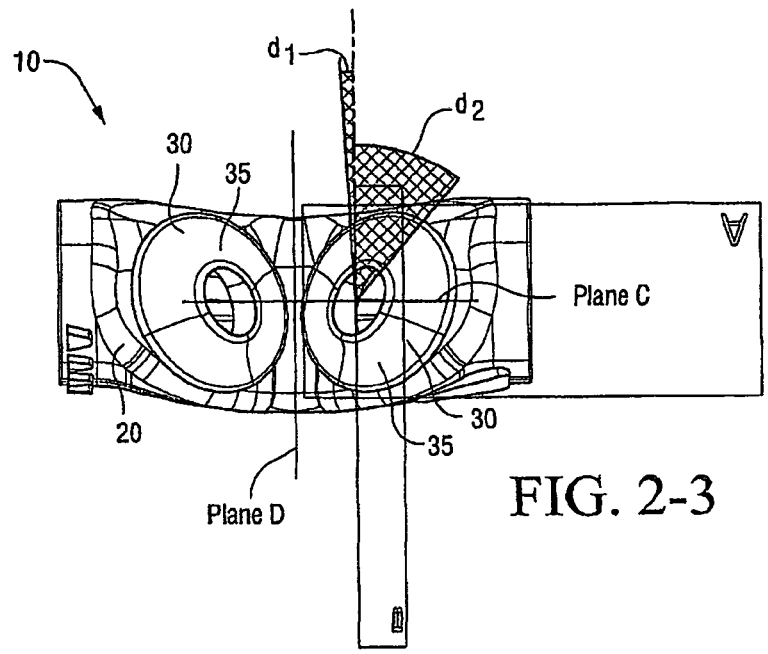

FIGS. 3-1 to 3-3 illustrate a nasal prong assembly 210 according to an embodiment of the present invention. As illustrated, each prong 230 includes a hood 260, e.g., integrally formed with the head portion 235.

The hood 260 is provided to an anterior portion (i.e., front portion) of the head portion 235 along the perimeter of the prong orifice. The hood 260 is structured to change the air flow in two planes such that the hood 260 directs the air flow away from the septum and towards the back of the patient's head (e.g., see FIG. 2-6).

As shown in FIG. 3-2, the hood 260 directs the air superiorly (indicated in solid lines), e.g., straight up such that the air flow paths are generally parallel to one another, rather than towards the septum as in the old configuration (indicated in dashed lines). In addition, as shown in FIG. 3-3, the hood 260 directs the air posteriorly (indicated in solid lines), e.g., towards the rear, rather than straight up the nasal passage as in the old configuration (indicated in dashed lines). This arrangement avoids direct contact with sensitive areas of the anterior nose.

2.1.2 Medial Hoods

Figures 2, 3, 4:
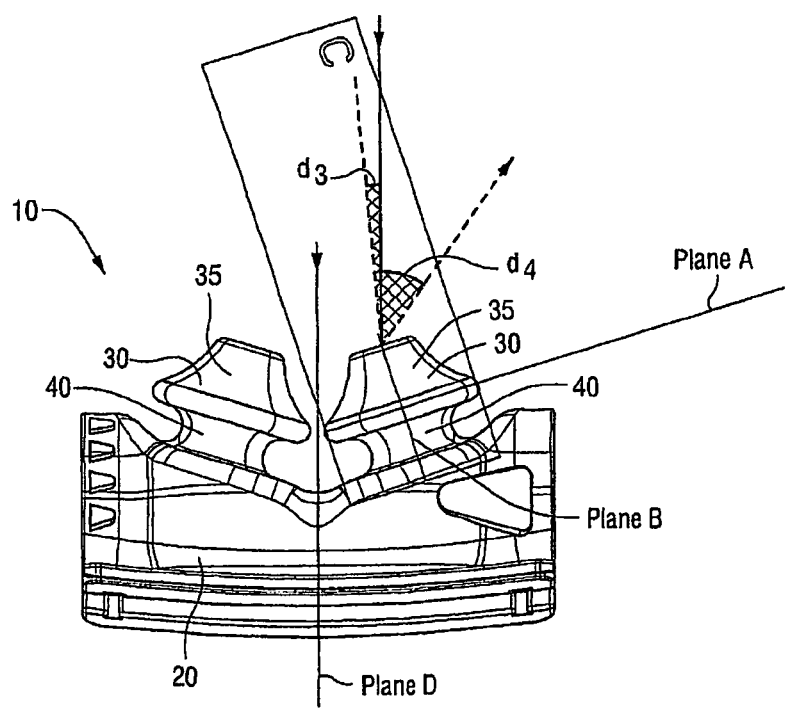

FIGS. 4-1 to 4-2 illustrate a nasal prong assembly 310 according to another embodiment of the present invention. As illustrated, each prong 330 includes a hood 360, e.g., integrally formed with the head portion 335.

The hood 360 is provided to an medial portion (i.e., middle portion) of the head portion 335 along the perimeter of the prong orifice. In the example of FIGS. 4-1 to 4-2, the hoods are provided on that portion of the prong closest to the other prong. The hood 360 is structured to change the air flow such that the hood 360 directs the air flow away from the septum.

As shown in FIG. 4-2, the hood 360 directs the air posteriorly (indicated in solid lines), e.g., straight up, rather than towards the septum as in the old configuration (indicated in dashed lines).

2.1.3 Large Hoods

Figures 2, 3, 4, 5:
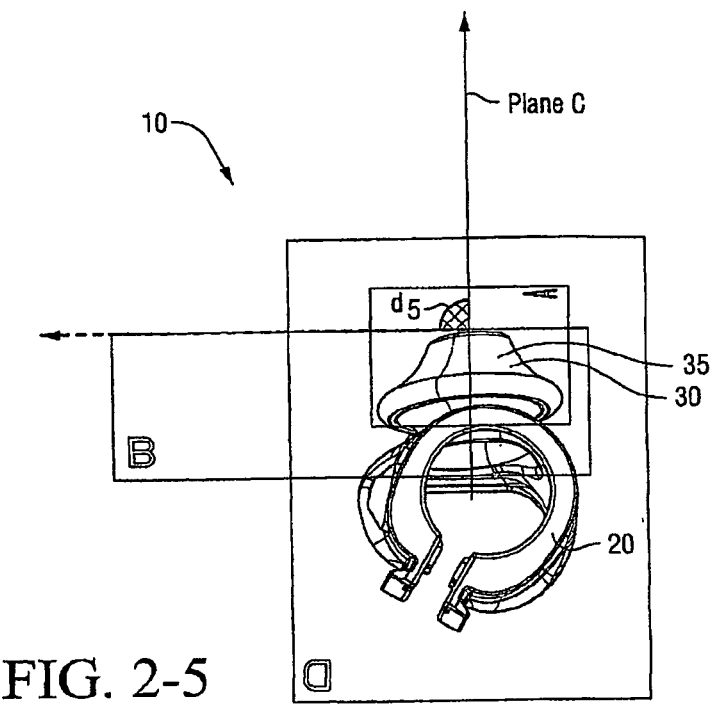

FIG. 5-1 illustrates a nasal prong assembly 410 according to another embodiment of the present invention. As illustrated, each prong 430 includes a hood 460, e.g., integrally formed with the head portion 435.

The hood 460 is a larger version of the hood 360 shown in FIG. 4-1. The hood 460 is structured to change the air flow such that the hood 460 directs the air flow away from the septum. The hood 460 may also protect sensitive areas of the anterior nose.

2.2 Shifted Orifice to Direct Air

The placement of the prong orifice may be changed or shifted (with respect to the orifice in the old configuration) to direct air flow. That is, the shifted orifice changes the air flow direction (with respect to the old configuration) to reduce and/or eliminate the air jetting effect.

For example, the prong orifice may be shifted such that its axis is offset from the axis of the prong, e.g., shifted orifice provided along the perimeter of the old orifice. The orifice position may be customized to a specific patient, e.g., placement based on patient preference or comfort. Also, the shifted orifice may facilitate locating the prong into the patient's nose.

In alternative embodiments, the prong orifice may be positioned anywhere along the perimeter of old orifice to eliminate and/or reduce the jetting effect, e.g., depending on the geometry of the patient's nares.

2.2.1 Posteriorly Shifted Orifice

Figures 2, 3, 4, 5, 6:
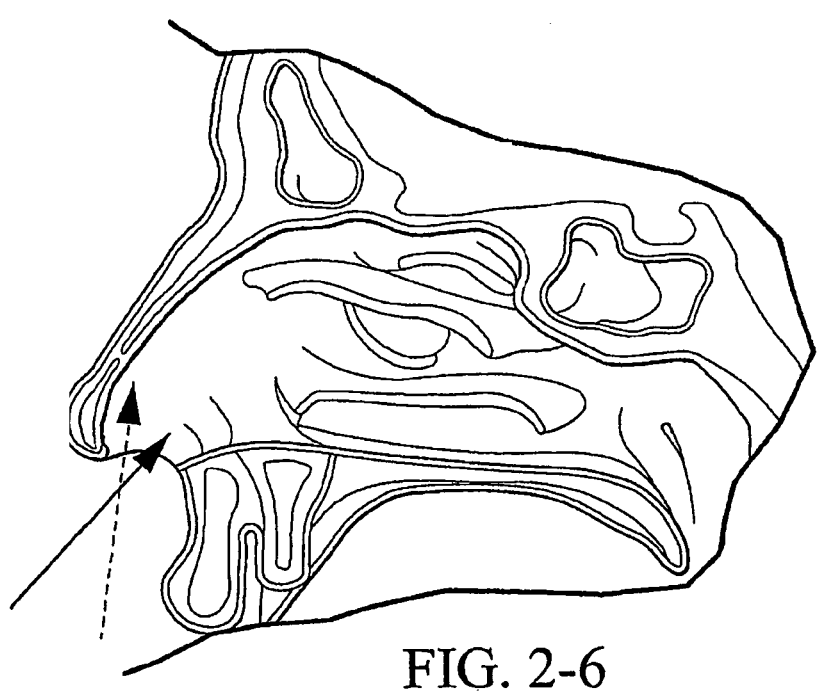
Figures 1, 3:
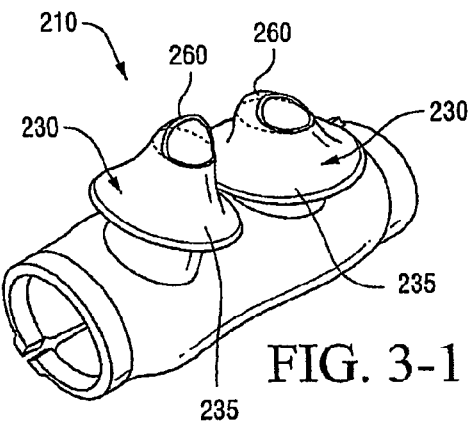
Figures 2, 3:
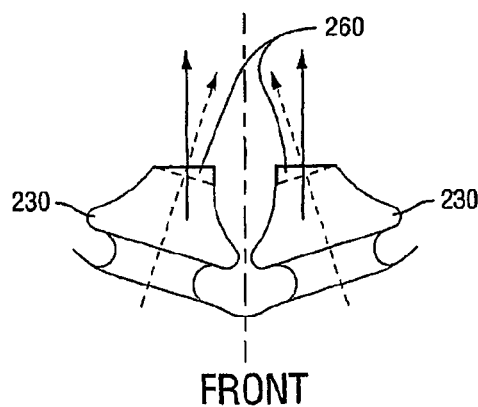
Figure 3:
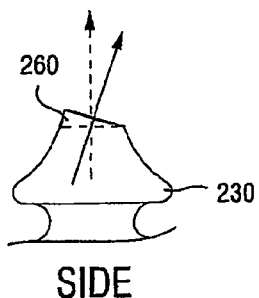

FIG. 6-1 illustrates a nasal prong assembly 510 according to another embodiment of the present invention. As illustrated, each prong 530 includes an orifice 545 that is shifted posteriorly towards the rear of the head portion 535 (with respect to the orifice in the old configuration shown in FIG. 1).

The posteriorly shifted orifice 545 is structured to shift the air flow more posteriorly as well as direct the air flow more posteriorly, e.g., towards the back of the patient's head rather than straight up the nasal passage as in the old configuration. This arrangement protects sensitive areas of the anterior nose.

2.2.2 Tiny Posterior Orifices

Figures 1, 7:
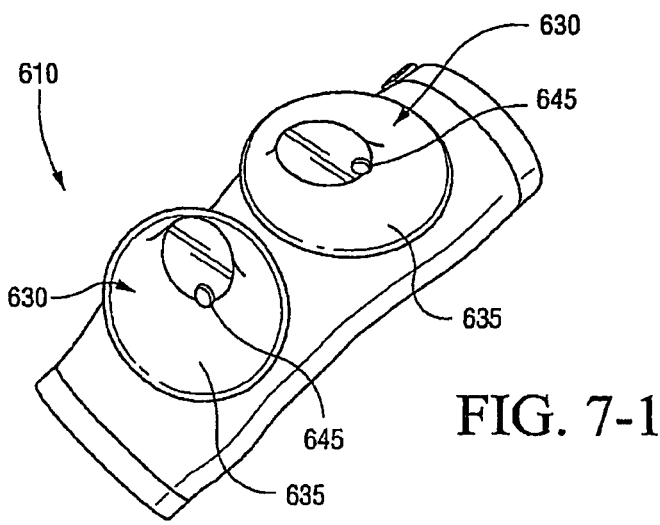

FIG. 7-1 illustrates a nasal prong assembly 610 according to another embodiment of the present invention. As illustrated, each prong 630 includes an orifice 645 that is shifted posteriorly towards the rear of the head portion 635 (with respect to the old orifice).

The posteriorly shifted orifice 645 is structured to shift the air flow more posteriorly as well as direct the air flow more posteriorly, e.g., towards the back of the patient's head rather than straight up the nasal passage as in the old configuration. In addition, the orifice 645 is relatively small to provide a relatively small concentrated jet of air directed posteriorly.

2.2.3 Medium Posterior Orifices

Figures 1, 8:
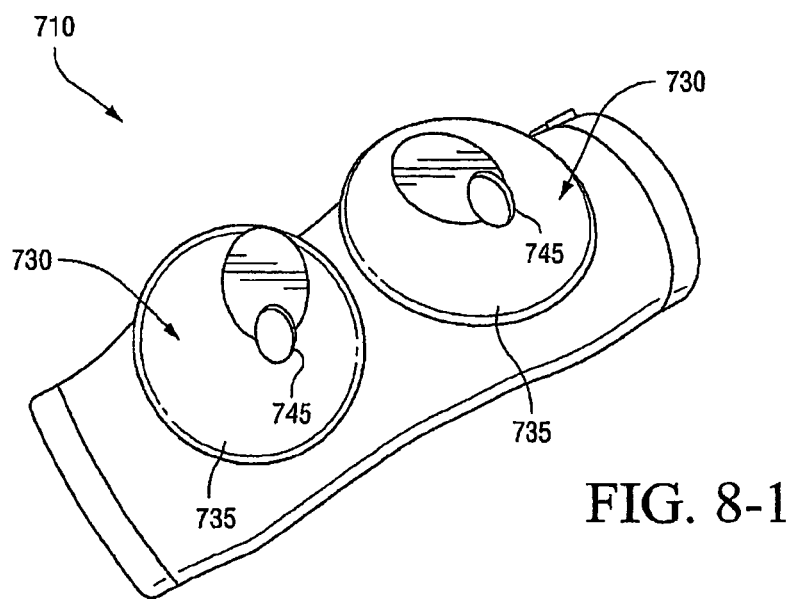

FIG. 8-1 illustrates a nasal prong assembly 710 according to another embodiment of the present invention. As illustrated, each prong 730 includes an orifice 745 that is shifted posteriorly towards the rear of the head portion 735 (with respect to the old orifice).

The posteriorly shifted orifice 745 is structured to shift the air flow more posteriorly as well as direct the air flow more posteriorly, e.g., towards the back of the patient's head rather than straight up the nasal passage as in the old configuration. The orifice 745 is medium sized (e.g., larger than the small orifice 645) to increase the available air flow and to provide a slightly more dispersed air flow.

2.3 Ribbing for Turbulence

Ribbing may be provided to the head portion of the nasal prong to create turbulence or a vortex. The ribbing creates turbulence in the air flow to reduce and/or eliminate the air jetting effect, e.g., air flow dispersed and not localized. That is, the ribbing disperses the air before it enters the patient's nasal cavity to reduce irritation.

Also, turbulence provides greater vapor or moisture exchange, which reduces dryness in the patient's nasal cavity. Specifically, turbulent flow may be more comfortable as dryness is reduced and humidity is increased because the humid air has more contact with the patient's nasal cavity rather than localized, directed flow.

In an alternative embodiment, turbulent flow may be created by a rotatable element within the nasal prong assembly, e.g., fan to create turbulence.

2.3.1 Helical Ribs

Figures 1, 9:
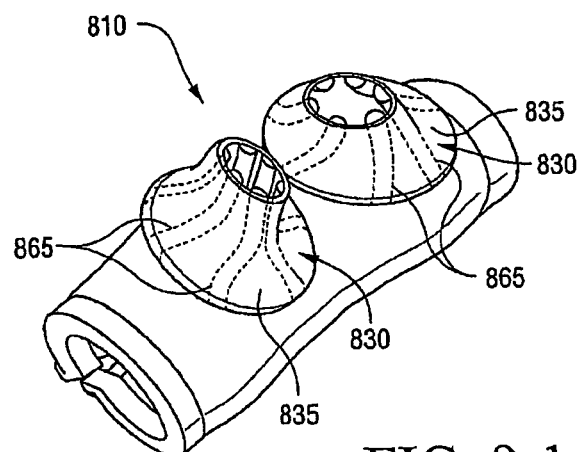
Figures 2, 9:
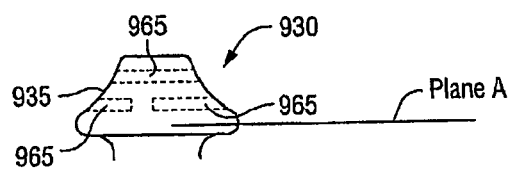

FIG. 9-1 illustrates a nasal prong assembly 810 according to another embodiment of the present invention. As illustrated, each prong 830 includes one or more ribs 865 that extend along an interior surface of the head portion 835, e.g., integrally formed with the head portion 835.

In the illustrated embodiment, each rib 865 has a helical shape that extends from the prong orifice to the rib or base of the head portion 835. However, the ribs may have other suitable shapes, and may have other suitable arrangements along the interior surface of the head portion 835, e.g., extend along a portion of the length of the head portion. As illustrated, 6 ribs 865 are provided to each prong 830. However, each prong 830 may have any suitable number of ribs, e.g., 1, 2, 3, 4, or 5 ribs.

In use, the helical ribs 865 introduce swirl to the air flow, which increase the dispersion and turbulence of the air as it exits the prong orifice.

2.3.2 Concentric Ribs

FIG. 9-2 illustrates a nasal prong 930 according to another embodiment of the present invention. As illustrated, the prong 930 includes a plurality of ribs 965 that form concentric ribs or rings along an interior surface of the head portion 935, e.g., integrally formed with the head portion 935.

In the illustrated embodiment, each rib 965 has a generally circular, oval, and/or arcuate shape that extends around at least a portion of the interior perimeter of the head portion 935. For example, some ribs 965 may extend around the entire interior perimeter of the head portion 935, and other ribs 965 may extend around portions of the interior perimeter of the head portion 935 (e.g., multiple ribs spaced around perimeter). The ribs 965 may be parallel and/or angled with respect to plane A shown in FIG. 2-4 (FIG. 9-2 shows ribs 965 parallel with plane A).

As illustrated, 3 ribs 965 are provided to the prong 930. However, the prong 930 may have any suitable number of ribs, e.g., 4 or 5 ribs.

In use, the ribs 965 increase the dispersion and turbulence of the air as it exits the prong orifice.

2.3.3 Non-Uniform Ribbing

Figures 1, 10:
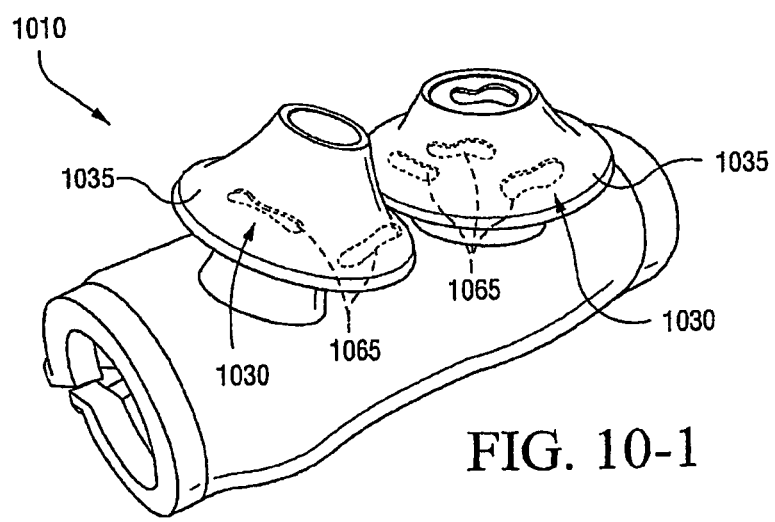

FIG. 10-1 illustrates a nasal prong assembly 1010 according to another embodiment of the present invention. As illustrated, each prong 1030 includes a plurality of ribs 1065 provided to an interior surface of the head portion 1035, e.g., integrally formed with the head portion 1035.

In the illustrated embodiment, each rib 1065 has a random or non-uniform shape that extends along a portion of the interior surface of the head portion 1035. Any suitable number of ribs 1065 may be provided to each prong 1030, e.g., 3, 4, 5 or more ribs.

In use, the ribs 1065 increase the dispersion and turbulence of the air as it exits the prong orifice.

2.3.4 Roughened Interior Surface

In an alternative embodiment, each prong may include a head portion with a roughened or coarsened interior surface. In use, the roughened interior surface may increase the dispersion and turbulence of the air as it exits the prong orifice.

2.4 Triangular Orifice for Turbulence

The shape of the prong orifice may be changed to create turbulence. In the illustrated embodiments described below, the prong orifice is changed from a generally oval shape in the old configuration to a triangular shape, e.g., equilateral or other triangular shape. However, other shapes are possible, e.g., square, hexagonal.

The triangular orifice may assume different positions or orientations, e.g., change location of triangle's apex. The orientation may affect air flow direction, and may be selected based on patient preference or comfort, e.g., so air flow is not directed to sensitive regions of the patient's nose.

2.4.1 Triangle with Anterior Apex

Figures 1, 11:
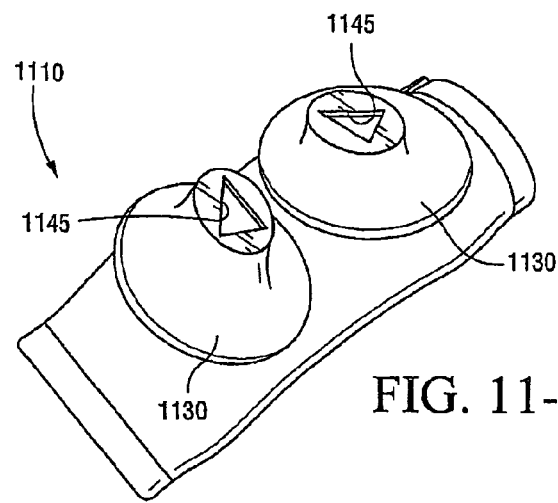
Figures 2, 11:
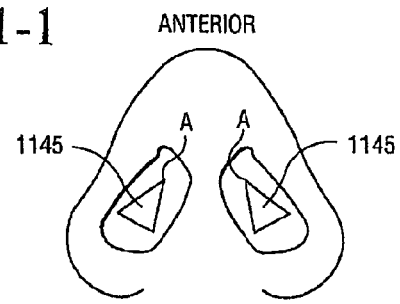

FIGS. 11-1 to 11-2 illustrate a nasal prong assembly 1110 according to another embodiment of the present invention. As illustrated, each prong 1130 includes an orifice 1145 with a triangular shape.

In the illustrated embodiment, the triangular orifice 1145 has an isosceles shape with the apex A oriented towards the anterior portion of the patient's nose (e.g., see FIG. 11-2). However, the triangular orifice 1145 may have other suitable shapes, e.g., equilateral or other triangular shape.

In use, the triangular orifice 1145 increases the dispersion and turbulence of the air as it exits the orifice and enters the patient's nasal passage. Specifically, the triangular orifice 1145 provides turbulent flow at its straight edges (slower air flow) and laminar flow at its vertices (faster air flow).

2.4.2 Triangle with Posterior Apex

Figures 1, 12:
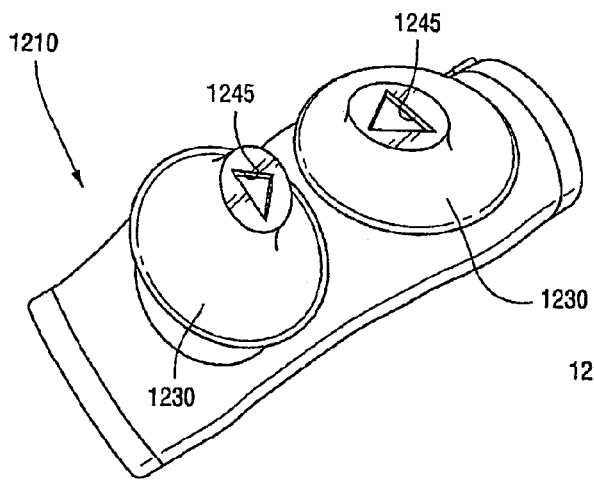
Figures 2, 12:
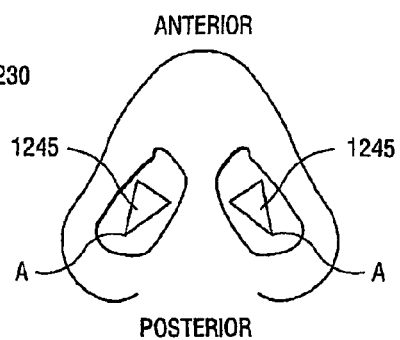

FIGS. 12-1 to 12-2 illustrate a nasal prong assembly 1210 according to another embodiment of the present invention. As illustrated, each prong 1230 includes an orifice 1245 with a triangular shape.

In the illustrated embodiment, the triangular orifice 1245 has an isosceles shape with the apex A oriented towards the posterior portion of the patient's nose (e.g., see FIG. 12-2). However, the triangular orifice 1245 may have other suitable shapes, e.g., equilateral or other triangular shape.

In use, the triangular orifice 1245 increases the dispersion and turbulence of the air as it exits the orifice and enters the patient's nasal passage. Specifically, the triangular orifice 1245 provides turbulent flow at its straight edges (slower air flow) and laminar flow at its vertices (faster air flow).

The orientation of the triangular orifice 1245 may be more preferable than that of the triangular orifice 1145 as the apex location provides flow that may avoid the septum.

2.5 Grate for Turbulence

A grate or grill may be provided to the nasal prong to create turbulence. The grate creates turbulence in the air flow to reduce and/or eliminate the air jetting effect, e.g., air flow dispersed and not localized. That is, the grate disperses the air before it enters the patient's nasal cavity to reduce irritation.

The grate may be provided at any suitable location along the nasal prong, e.g., at the base of the stalk, at the rim of nasal portion, etc. In addition, the grates of the grate may have any suitable shape and orientation.

The grate may be formed with a material similar to the prong, e.g., silicone. In alternative embodiments, the grate may be formed with Gortex or a textile membrane.

2.5.1 Grate Parallel to Minor Axis of Orifice

Figures 1, 13:
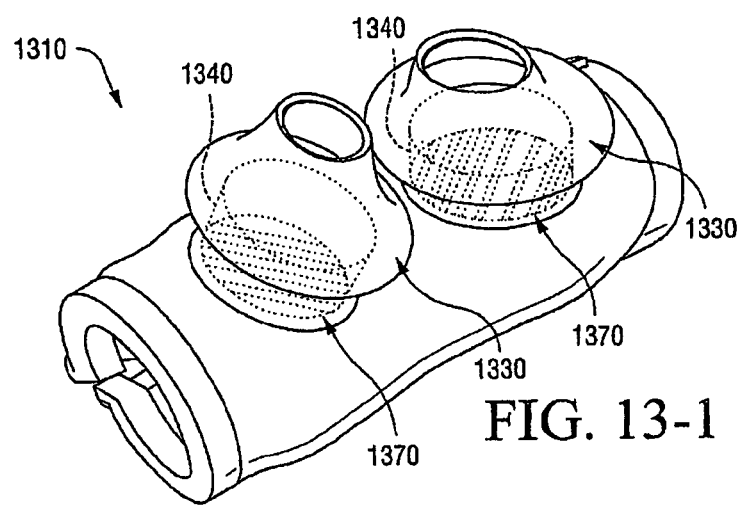
Figures 2, 13:
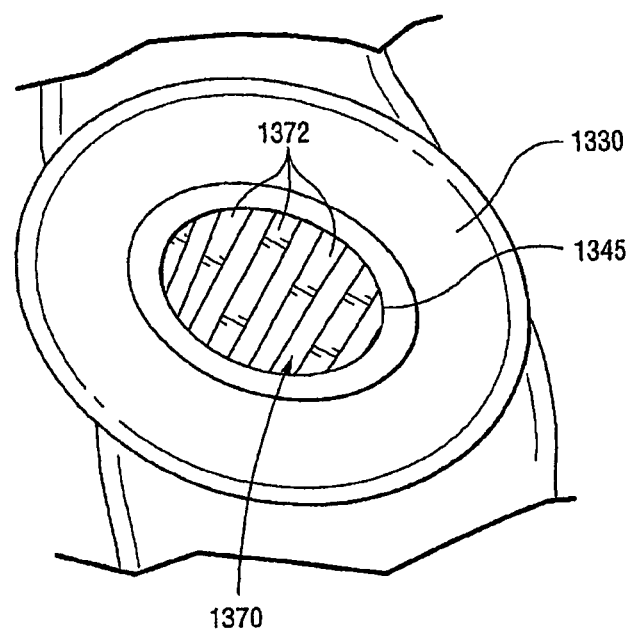

FIGS. 13-1 to 13-2 illustrate a nasal prong assembly 1310 according to another embodiment of the present invention. As illustrated, each prong 1330 includes a grate 1370 along an interior portion of the prong 1330, e.g., integrally formed with the prong 1330.

In the illustrated embodiment, the grate 1370 is provided at the base of the stalk 1340 of the prong 1330. Also, the grate 1370 is oriented such that the grates 1372 of the grate 1370 extend generally parallel to the minor axis of the prong orifice 1345 (e.g., see FIG. 13-2). However, the grate 1370 may be provided at other suitable locations along the prong, and the grates 1372 may have other suitable shapes and orientations. In addition, the grate 1370 may have any suitable number of grates 1372, e.g., 3, 4, 5, or more grates.

In use, the grate 1370 increases the dispersion and turbulence of the air as it exits the prong orifice and enters the patient's nasal passage.

2.5.2 Grate Parallel to Major Axis of Orifice

Figures 1, 14:
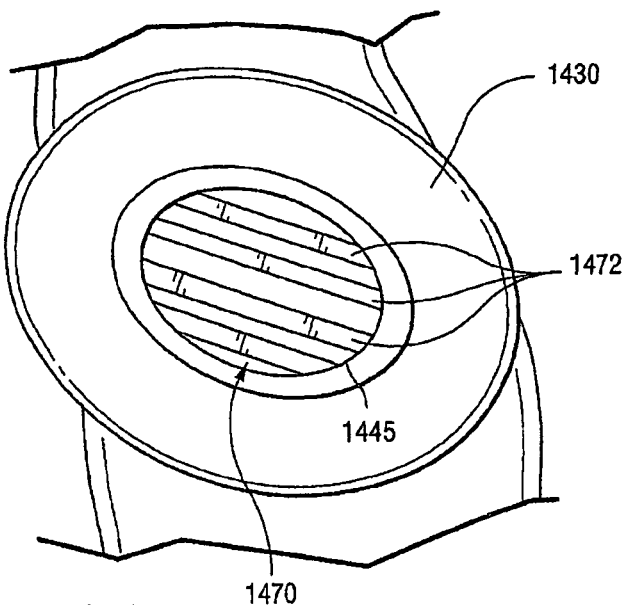

FIG. 14-1 illustrates a nasal prong 1430 including a grate 1470 according to another embodiment of the present invention. The grate 1470 is substantially similar to the grate 1370 described above, e.g., grate 1470 is provided at the base of the stalk of the prong 1430. In contrast, the grate 1470 is oriented such that the grates 1472 of the grate 1470 extend generally parallel to the major axis of the prong orifice 1445. However, the grate 1470 may be provided at other suitable locations along the prong, and the grates 1472 may have other suitable shapes and orientations. In addition, the grate 1470 may have any suitable number of grates 1472, e.g., 3, 4, 5, or more grates.

In use, the grate 1470 increases the dispersion and turbulence of the air as it exits the prong orifice and enters the patient's nasal passage.

2.5.3 Circular Grate

Figures 1, 15:
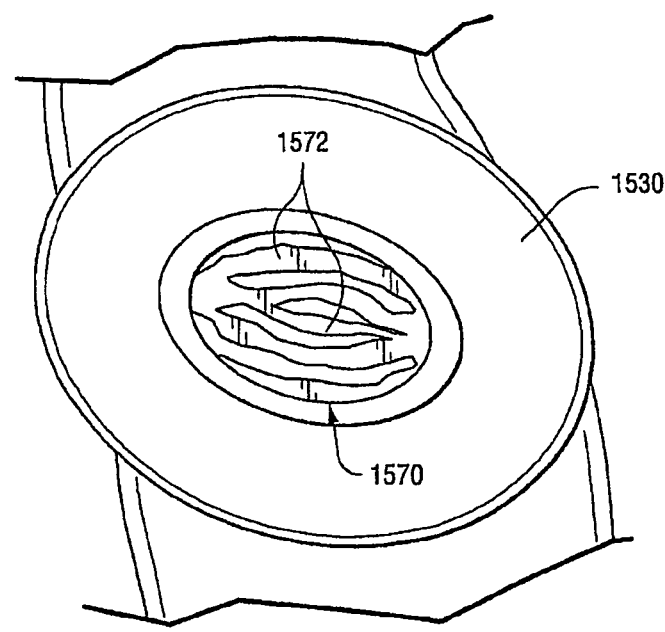

FIG. 15-1 illustrates a nasal prong 1530 including a grate 1570 according to another embodiment of the present invention. As illustrated, the grates 1572 of the grate 1570 have a generally oval or circular configuration, e.g., grates 1572 are curved or arcuate and define one or more generally circular or oval openings through the grate.

The grate 1570 may be provided at the base of the stalk of the prong 1530, or at other suitable locations along the prong. Also, the grates 1572 may have other suitable shapes and orientations. In addition, the grate 1570 may have any suitable number of grates 1572, e.g., 3, 4, 5, or more grates.

In use, the grate 1570 increases the dispersion and turbulence of the air as it exits the prong orifice and enters the patient's nasal passage.

2.5.4 Grate at Rim of Prong

Figures 1, 16:
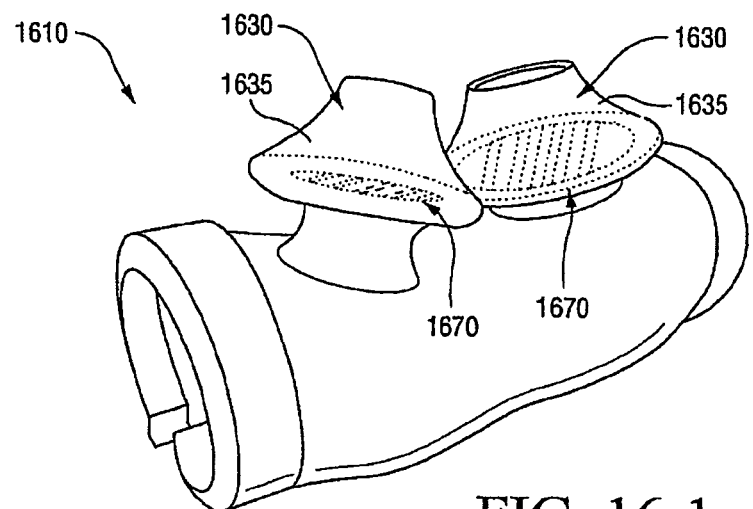
Figures 2, 16:
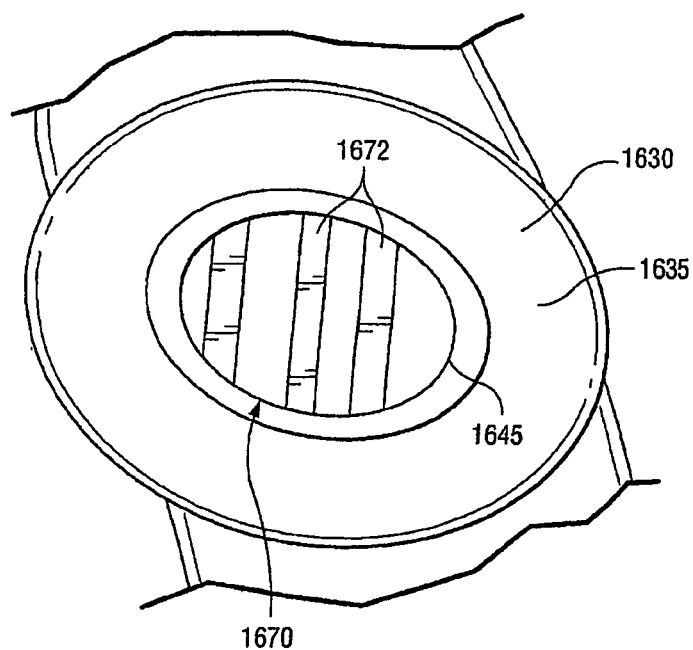

FIGS. 16-1 to 16-2 illustrate a nasal prong assembly 1610 according to another embodiment of the present invention. As illustrated, each prong 1630 includes a grate 1670 along an interior portion of the prong 1630, e.g., integrally formed with the prong 1630.

In the illustrated embodiment, the grate 1670 is provided at the rim of the head portion 1635 of the prong 1630. Also, the grate 1670 is oriented such that the grates 1672 of the grate 1670 extend generally parallel to the minor axis of the prong orifice 1645 (e.g., see FIG. 16-2). However, the grate 1670 may be provided at other suitable locations along the prong, and the grates 1672 may have other suitable shapes and orientations. In addition, the grate 1670 may have any suitable number of grates 1672, e.g., 3, 4, 5, or more grates.

In use, the grate 1670 increases the dispersion and turbulence of the air as it exits the prong orifice and enters the patient's nasal passage.

2.5.5 Medial Hoods with Grates

Figures 1, 17:
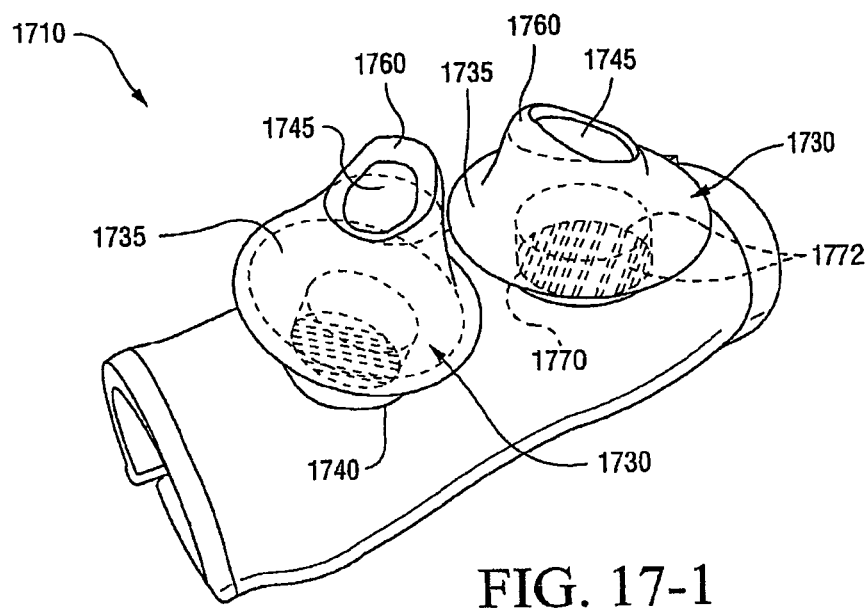

FIG. 17-1 illustrates a nasal prong assembly 1710 according to another embodiment of the present invention. The nasal prong assembly 1710 is a hybrid or combination of the nasal prong assemblies shown in FIGS. 4-1 to 4-2 and 13-1 to 13-2. Specifically, each prong 1730 includes a hood 1760 and a grate 1770, e.g., integrally formed with the prong 1730.

As illustrated, the hood 1760 is provided to an medial portion (i.e., middle portion) of the head portion 1735 and is structured to re-direct the air flow such that the hood 1760 directs or channels the air flow away from the septum.

The grate 1770 is provided at the base of the stalk 1740 of the prong 1730. Also, the grate 1770 is oriented such that the grates 1772 of the grate 1770 extend generally parallel to the minor axis of the prong orifice 1745. However, the grate 1770 may be provided at other suitable locations along the prong, and the grates 1772 may have other suitable shapes and orientations. In addition, the grate 1770 may have any suitable number of grates 1772, e.g., 3, 4, 5, or more grates.

In use, the hood 1760 directs the air posteriorly (e.g., straight up) away from the septum and the grate 1770 increases the dispersion and turbulence of the air as it exits the prong orifice and enters the patient's nasal passage. Thus, the air flow is both dispersed and channeled away from the septum.

2.5.6 Large Hoods with Grates

Figures 1, 18:
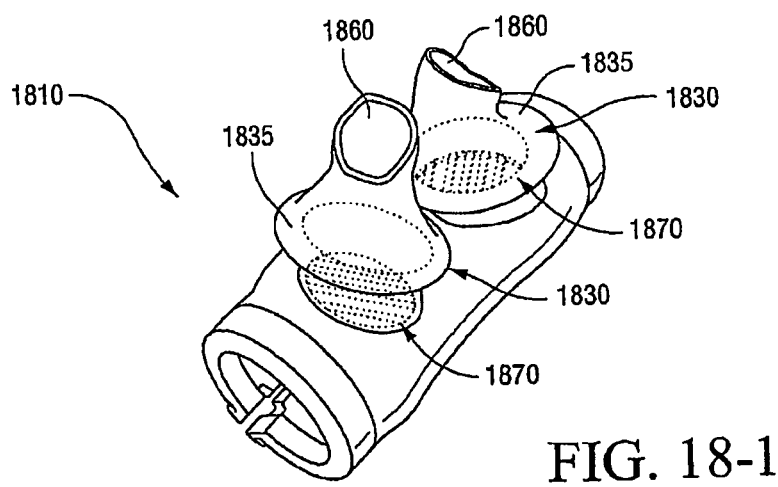
Figures 2, 18:
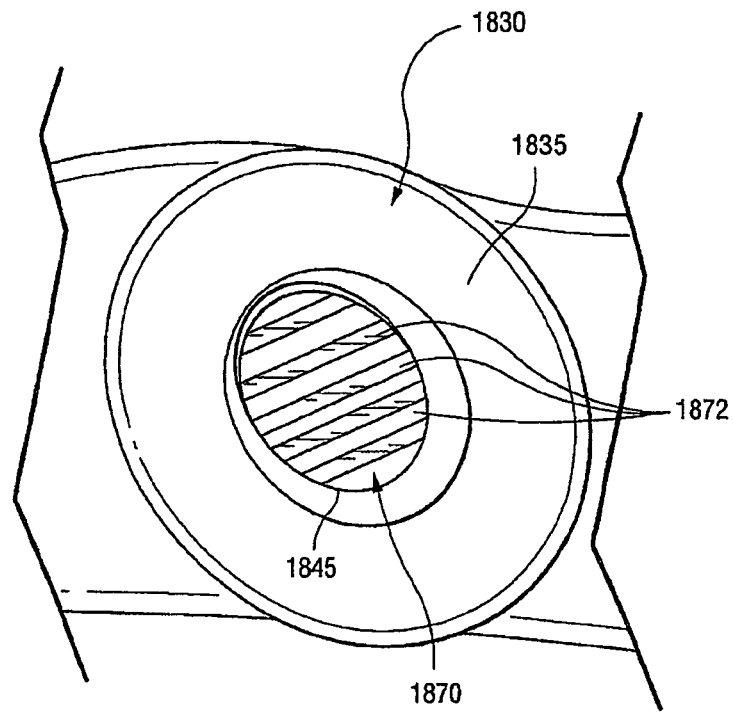

FIG. 18-1 to 18-2 illustrate a nasal prong assembly 1810 according to another embodiment of the present invention. The nasal prong assembly 1810 is a hybrid or combination of the nasal prong assemblies shown in FIGS. 5-1 and 13-1 to 13-2. Specifically, each prong 1830 includes a relatively large hood 1860 and a grate 1870, e.g., integrally formed with the prong 1830.

As illustrated, the hood 1860 is provided to an medial portion (i.e., middle portion) of the head portion 1835 and is structured to change the air flow such that the hood 1860 directs the air flow away from the septum.

The grate 1870 is provided at the base of the stalk 1840 of the prong 1830. Also, the grate 1870 is oriented such that the grates 1872 of the grate 1870 extend generally parallel to the minor axis of the prong orifice 1845 (e.g., see FIG. 18-2). However, the grate 1870 may be provided at other suitable locations along the prong, and the grates 1872 may have other suitable shapes and orientations. In addition, the grate 1870 may have any suitable number of grates 1872, e.g., 3, 4, 5, or more grates.

In use, the hood 1860 directs the air posteriorly (e.g., straight up) away from the septum and the grate 1870 increases the dispersion and turbulence of the air as it exits the prong orifice and enters the patient's nasal passage. Thus, the air flow is both dispersed and away from the septum. The hood 1860 may also protect sensitive areas of the anterior nose.

2.6 Dual Wall

The nasal prong may have a dual or double-wall head portion, i.e., a head portion including an inner wall (inner membrane) and an outer wall (outer membrane) that surrounds the inner wall. Such an arrangement may enhance the comfort and/or seal of the prong.

Embodiments of dual-wall nasal prongs are disclosed in PCT Appln. Nos. PCT/AU2004/001832 and PCT/AU2006/000770, each of which is incorporated herein by reference in its entirety. The illustrated embodiments described below include features that may be used with the embodiments and/or components described in these incorporated PCT applications.

2.6.1 Dual Wall Embodiment

Figures 1, 19:
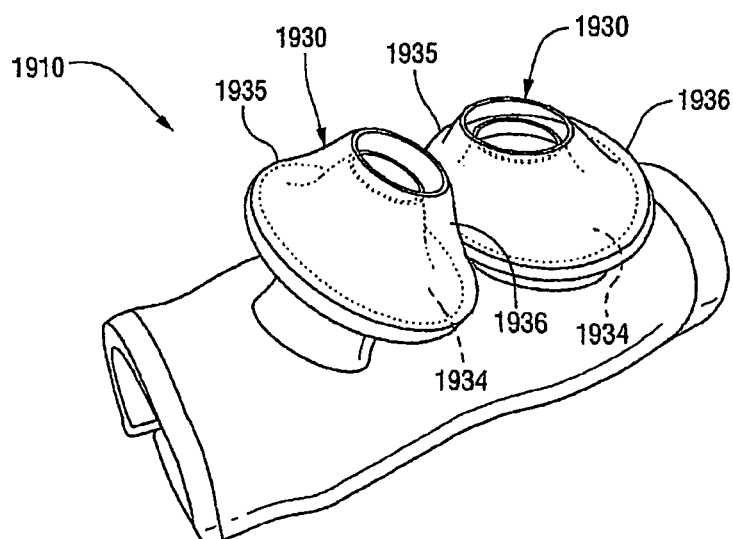

FIG. 19-1 illustrates a nasal prong assembly 1910 according to another embodiment of the present invention. As illustrated, each prong 1930 includes dual or double-wall head portion 1935. Specifically, each head portion 1935 includes an inner wall 1934 (inner membrane) and an outer wall 1936 (outer membrane) that surrounds the inner wall 1934.

The outer wall 1936 is relatively thin, e.g., thickness in the range of 0.1 mm to 0.65 mm, and provides compliance and/or conformance with the patient's nose to enhance the seal of the prong 1930.

Further details of such dual-wall head portion are provided in PCT Appln. No. PCT/AU2006/000770, for example.

2.6.2 Smaller Dual Wall

Figures 1, 20:
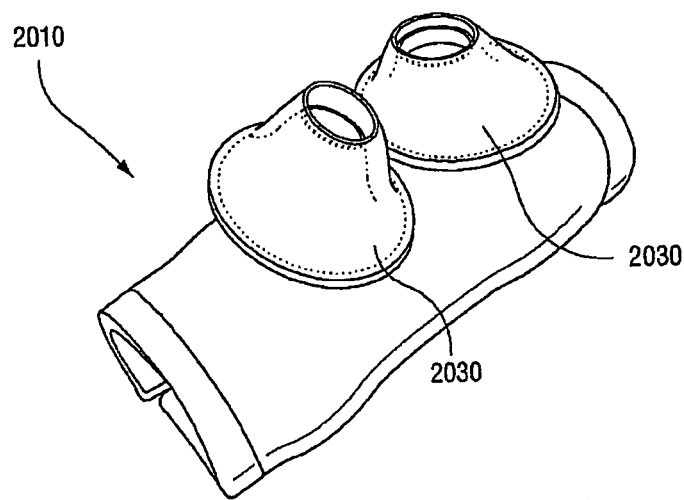

The dual-wall nasal prong may be provided in different sizes. For example, FIG. 20-1 illustrates a nasal prong assembly 2010 including dual-wall nasal prongs 2030 which are a smaller version of the dual-wall nasal prongs 1930 shown in FIG. 19-1. Such a smaller dual-wall nasal prong 2030 may provide a more comfortable fit and/or seal for some patients.

2.6.3 Dual Wall with Holes on Inner Wall

Figures 1, 21:
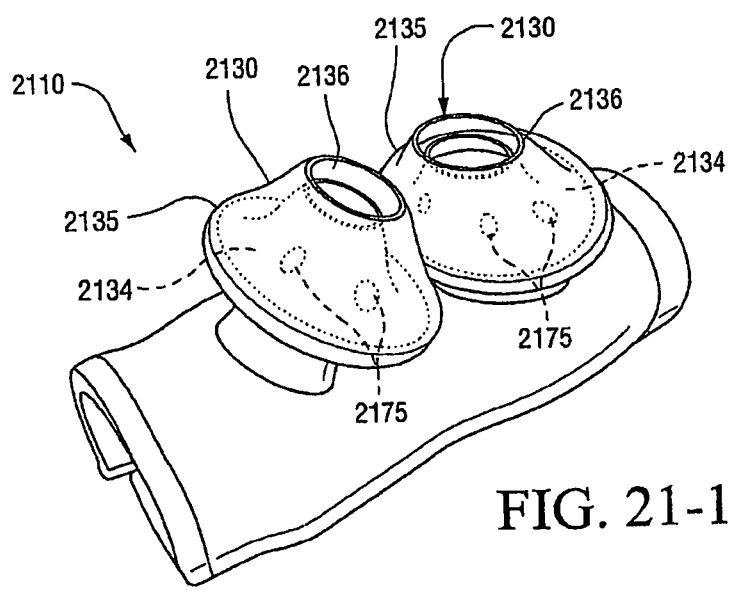

FIG. 21-1 illustrates a nasal prong assembly 2110 according to another embodiment of the present invention. As illustrated, each prong 2130 includes dual or double-wall head portion 2135. Specifically, each head portion 2135 includes an inner wall 2134 (inner membrane) and an outer wall 2136 (outer membrane) that surrounds the inner wall 2134.

In the illustrated embodiment, the inner wall 2134 includes a plurality of holes 2175. The holes 2175 may be provided along any suitable portion of the inner wall 2134. Also, the holes 2175 may be circular or may have any other suitable shapes, e.g., non-circular. In addition, the inner wall 2134 may have any suitable number of holes 2175, e.g., 3, 4, 5, or more holes.

In use, the holes 2175 disperse air as it passes through the prong 2130, e.g., to create turbulence.

2.6.4 Dual Wall with Grate

Figures 1, 22:
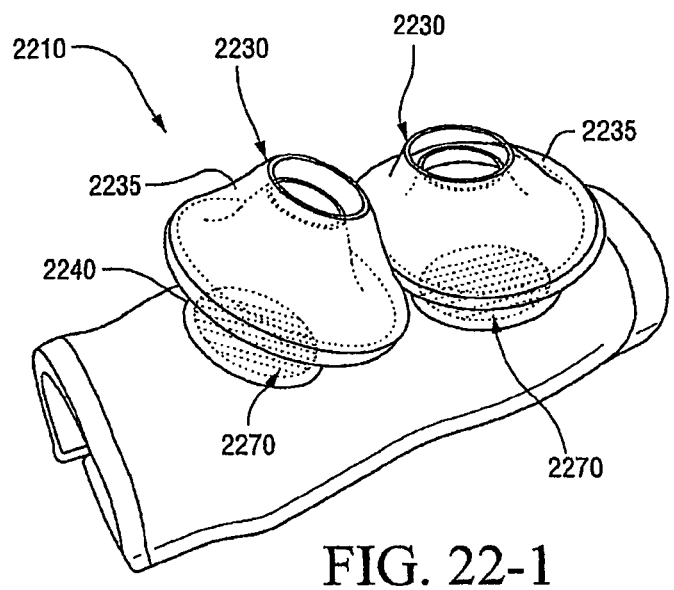
Figures 2, 22:
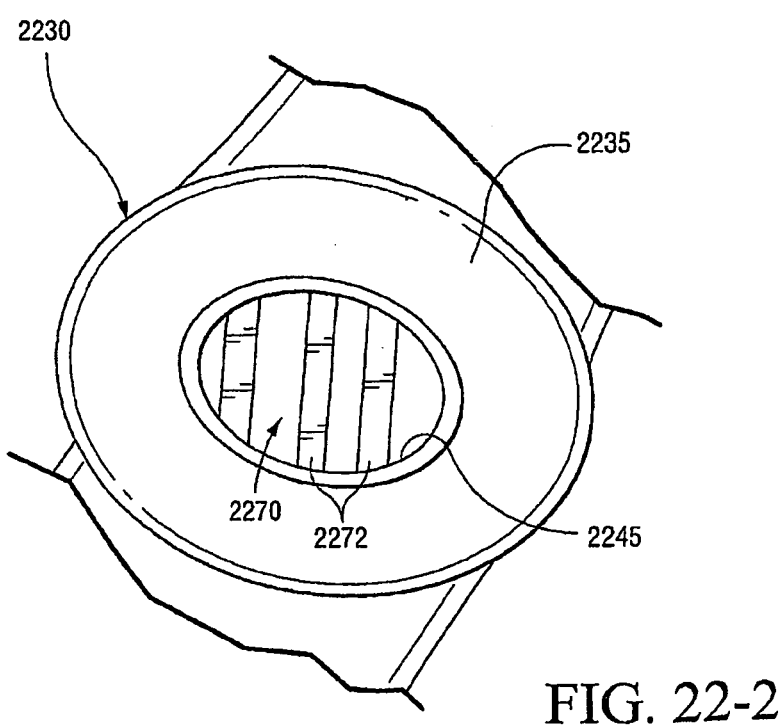

FIGS. 22-1 to 22-2 illustrate a nasal prong assembly 2210 according to another embodiment of the present invention. As illustrated, each prong 2230 includes dual or double-wall head portion 2235. In addition, each prong 2230 includes a grate 2270.

In the illustrated embodiment, the grate 2270 is provided at the base of the stalk 2240 of the prong 2230. Also, the grate 2270 is oriented such that the grates 2272 of the grate 2270 extend generally parallel to the minor axis of the prong orifice 2245 (e.g., see FIG. 22-2). However, the grate 2270 may be provided at other suitable locations along the prong, and the grates 2272 may have other suitable shapes and orientations. In addition, the grate 2270 may have any suitable number of grates 2272, e.g.; 3, 4, 5, or more grates.

In use, the dual-wall head portion 2235 increases comfort and/or seal and the grate 2270 increases the dispersion and turbulence of the air as it exits the prong orifice and enters the patient's nasal passage.

2.6.5 Dual Wall with Ribs

Figures 1, 23:
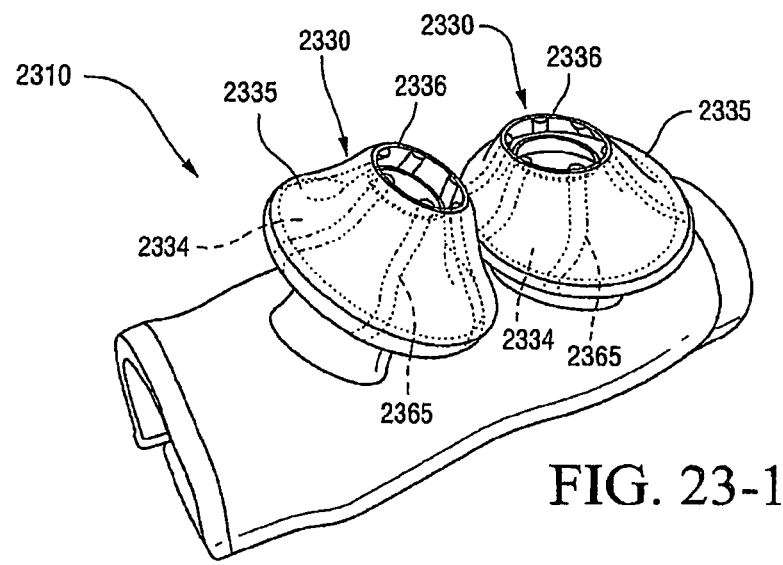
Figures 2, 23:
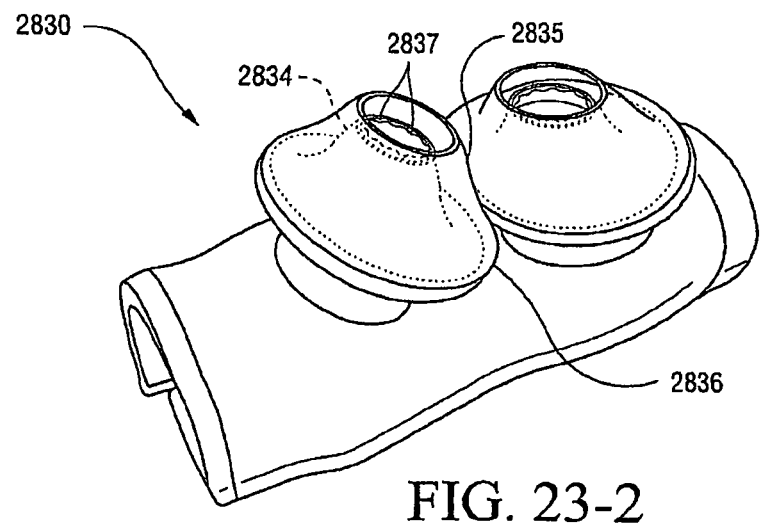
Figures 3, 23:
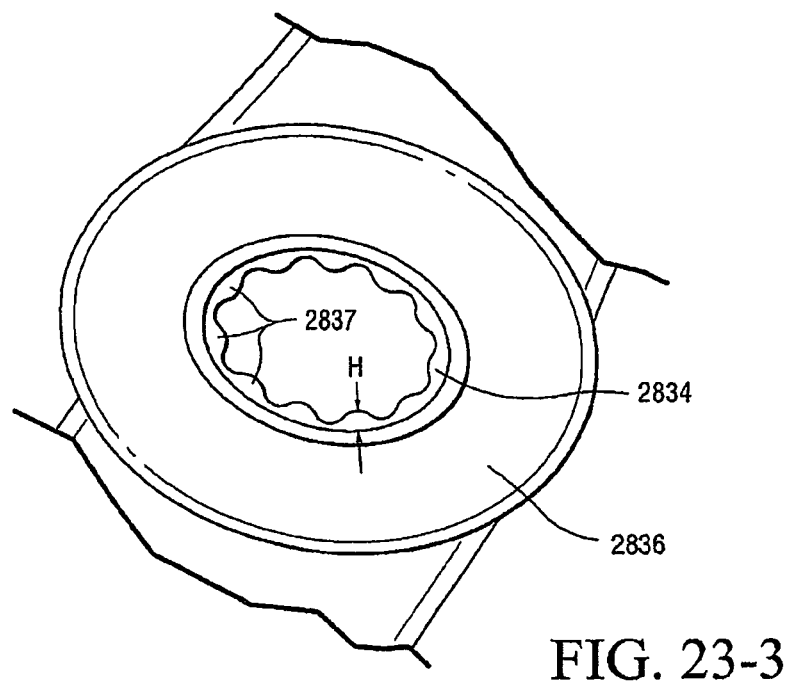

FIG. 23-1 illustrates a nasal prong assembly 2310 according to another embodiment of the present invention. As illustrated, each prong 2330 includes dual or double-wall head portion 2335. In addition, each prong 2330 includes a plurality of ribs 2365 that extend along an interior surface of the outer wall 2336.

In the illustrated embodiment, each rib 2365 has a helical shape that extends from the prong orifice to the rib or base of the head portion outer wall 2336. However, the ribs may have other suitable shapes, and may have other suitable arrangements along the outer wall 2336. As illustrated, 6 ribs 2365 are provided to each prong 2330. However, each prong 2330 may have any suitable number of ribs, e.g., 3, 4, or 5 ribs. Further, ribs may be provided to inner and/or outer surfaces of the inner wall 2334, e.g., in lieu of or in addition to the ribs on the outer wall 2336.

In use, the dual-wall head portion 2335 increases comfort and/or seal and the helical ribs 2365 introduce swirl to the air flow, which increase the dispersion and turbulence of the air as it exits the prong orifice and enters the patient's nasal passage.

FIGS. 23-2 and 23-3 illustrate a nasal prong 2830 according to another embodiment of the present invention. As illustrated, the prong 2830 includes a dual or double-wall head portion 2835. In addition, the orifice of the inner wall 2834 includes a series of contours or lobes 2837, e.g., 9 contours or lobes, each having a suitable height H. However, the inner wall 2834 may include any suitable number of contours or lobes, e.g., 3, 4, 5, 6, or more contours or lobes. Further, a series of contours or lobes may be provided to the orifice of the outer wall 2836.

In the illustrated embodiment, the series of contours or lobes 2837 extend within the plane of the orifice. In an alternative embodiment, one or more of the contours or lobes may extend in a plane that is transverse to the plane of the orifice.

In use, the series of contours or lobes 2837 provides a "jet engine like" diffuser or non-oval-shaped orifice which increases the dispersion and turbulence of the air as it exits the orifice and enters the patient's nasal passage.

2.6.6 Dual Wall with Lower Inner Wall

FIG. 24-1 illustrates a nasal prong assembly 2410 according to another embodiment of the present invention. As illustrated, each prong 2430 includes dual or double-wall head portion 2435. Specifically, each head portion 2435 includes an inner wall 2434 (inner membrane) and an outer wall 2436 (outer membrane) that surrounds the inner wall 2134.

In the illustrated embodiment, the orifice of the inner wall 2434 is substantially lower than the orifice of the outer wall 2436 (e.g., compared to the dual-wall prong shown in FIG. 19-1). Such an arrangement may create more diffuse air entering the nasal passage without compromising a seal.

2.6.7 Dual Wall with Hood

In an alternative embodiment, the dual wall prong may include a hood such as that shown in FIGS. 3-1 to 3-3 or 4-1 to 4-2. The hood may extend from the outer wall and/or the inner wall.

2.6.8 Dual Wall with Shifted Orifice

Figures 1, 25:
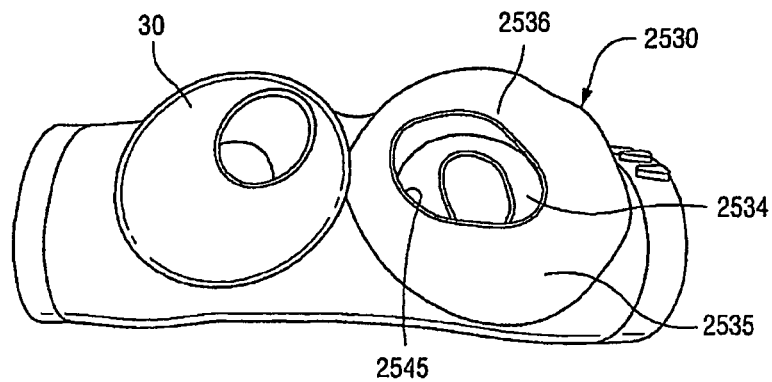

FIG. 25-1 illustrates a nasal prong 2530 according to another embodiment of the present invention. In the illustrated embodiment, the nasal prong 2530 is provided adjacent to a prong 30 of the old configuration for comparison purposes.

As illustrated, the prong 2530 includes dual or double-wall head portion 2535 with inner and outer walls 2534, 2536. In addition, the prong orifice 2545 is shifted more posteriorly and medially (with respect to the prong orifice of the old configuration), e.g., closer to the patient's lip. However, the prong orifice may be shifted to other suitable positions.

In use, the posteriorly shifted orifice 2545 is structured to shift the air flow more posteriorly and medially as well as direct the air flow more posteriorly and medially, e.g., direct air flow into the nasal passage as opposed to onto the nasal septum.

2.6.9 Dual Wall with Shifted Orifice, Hood, and Grate

In an alternative embodiment, the nasal prong 2530 of FIG. 25-1 may also include a hood (e.g., such as that shown in FIGS. 3-1 to 3-3 or 4-1 to 4-2), and a grate (e.g., such as that shown in FIG. 13-1).

In use, the hood directs the air away from the septum and/or towards the back of the patient's head the grate increases the dispersion and turbulence of the air as it exits the prong orifice and enters the patient's nasal passage.

2.7 Thin Membrane

In alternative embodiment, a thin wall thickness, e.g., thickness in the range of 0.1 mm to 0.65 mm, may be provided to a nasal prong having a single wall configuration. Further details of such thin single wall nasal prong is provided in PCT Appln. No. PCT/AU2006/000770, for example.

In an embodiment, ribs (e.g., such as that shown in FIG. 9-1, 9-2, or 10-1) may be provided to the thin single wall nasal prong.

2.8 Orifice Cut at an Angle

The orifice of the nasal prong may be cut at an angle (with respect to the prong orifice of the old configuration) to direct air flow similar to a hood. That is, the angled orifice changes the air flow direction (with respect to the old configuration) to reduce and/or eliminate the air jetting effect, e.g., direct flow away from the septum.

2.8.1 45° Cut Orifice

Figures 1, 26:
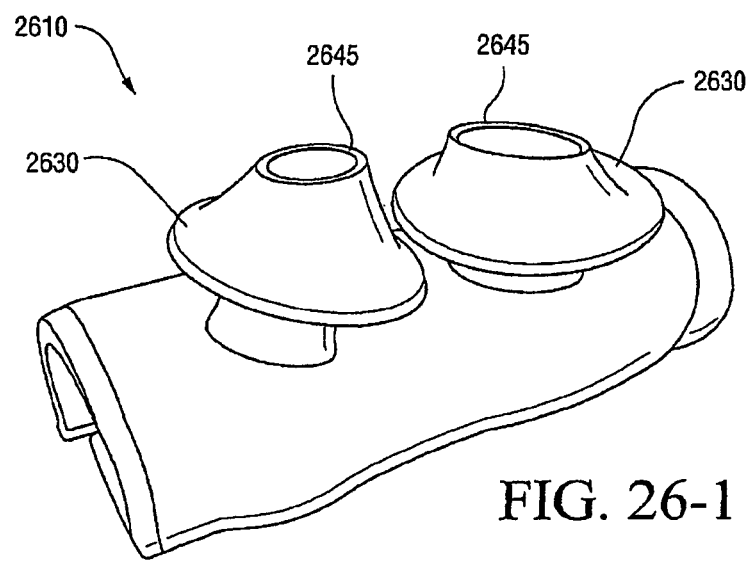
Figures 2, 26:
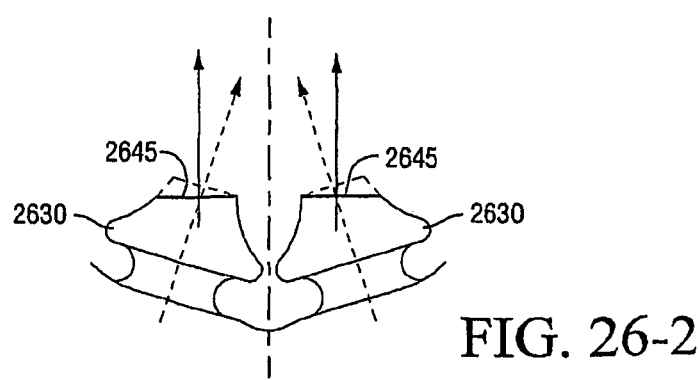

FIGS. 26-1 to 26-2 illustrate a nasal prong assembly 2610 according to another embodiment of the present invention. As illustrated, each prong 2630 includes a prong orifice 2645 that is cut at about a 45° angle (with respect to the prong orifice of the old configuration). However, the prong orifice 2645 may be cut at other suitable angles, e.g., angle may be dependent on the shape of the patient's nostrils.

The 45° cut prong orifice 2645 redirects air similar to a hood as described above, and maintains seal, integrity, and comfort. Specifically, as shown in FIG. 26-2, the 45° cut prong orifice 2645 is structured to direct the air superiorly (as indicated in solid lines), e.g., straight up, rather than towards the septum as in the old configuration (as indicated in dashed lines).

2.8.2 Dual Wall with Shifted Orifice and 45° Cut Orifice

In an alternative embodiment, the nasal prong 2530 of FIG. 25-1 may also include a 45° cut prong orifice (e.g., such as that shown in FIGS. 26-1 to 26-2).

In use, the 45° cut prong orifice 2645 directs the air superiorly away from the septum.

2.9 Concave Anterior Prong

Figures 1, 27:
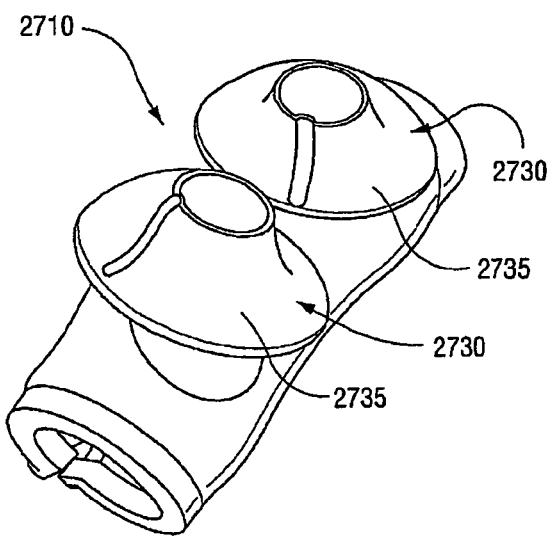
Figures 2, 27:
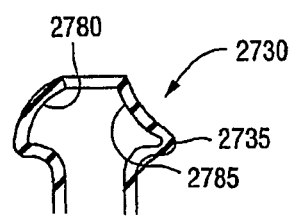

FIGS. 27-1 to 27-2 illustrate a nasal prong assembly 2710 according to another embodiment of the present invention. In the illustrated embodiment, the shape of an anterior portion of the prong 2730 is different than the shape of a posterior portion of the prong 2730.

Specifically, as best shown in FIG. 27-2, the anterior portion of the head portion 2735 has a concave shape or section 2780 (as viewed from the inside of the prong) and the posterior portion of the head portion 2735 has a convex shape or section 2785 (as viewed from the inside of the prong).

In use, the concave section 2780 of the head portion 2735 directs and disperses the air flow posteriorly, e.g., towards the back of the patient's head.

3. Dispersion Cartridge Provided to Nasal Prong Assembly

Figures 1, 28:
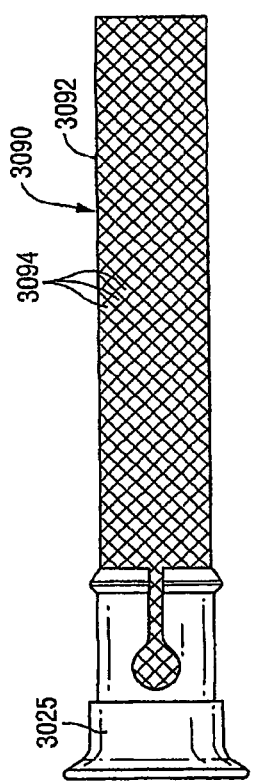
Figures 2, 28:
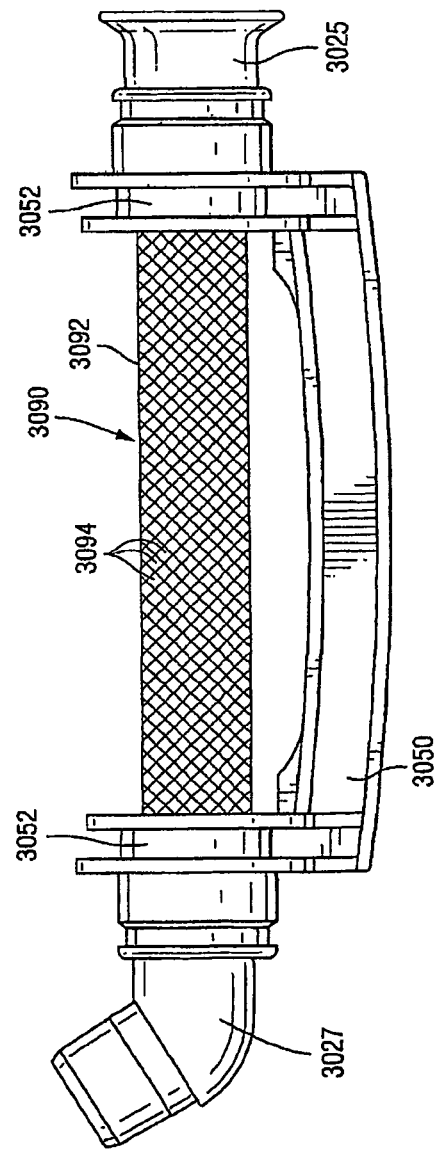

As shown in FIGS. 28-1 to 28-3, a disposable or reuseable gas dispersion cartridge 3090 may be provided to a nasal prong assembly to increase turbulence and/or decrease the velocity in the gas or air flow. As illustrated, the dispersion cartridge 3090 includes a plurality of openings that creates turbulence and/or decreases the velocity in the air flow to reduce and/or eliminate the air jetting effect. That is, the dispersion cartridge 3090 disperses the air before it enters the nasal prongs and hence patient's nasal cavity to reduce irritation.

Also, the dispersion cartridge 3090 is structured to reduce the velocity of air traveling into the nasal passage to provide comfort to the patient (e.g., see sections 2.3 and 2.4.1), reduce noise generated due to air velocity in the mask system, and reduce noise transmitted into the mask system from the flow generator.

In the illustrated embodiment, the dispersion cartridge 3090 is a single part that may be provided, e.g., retrofit, to an existing nasal prong assembly (such as that shown in FIG. 1). As illustrated, the dispersion cartridge 3090 includes a mesh-like cylinder 3092 that provides a plurality of openings or pores 3094 therethrough. As shown in FIG. 28-1, one end of the mesh-like cylinder 3092 is provided to an end plug 3025, e.g., removably or non-removably attached to the end plug, that is adapted to be attached to one end of the frame 3050. Further details of such end plug are described in the above incorporated U.S. patent application Ser. No. 11/101,657.

When the end plug 3025 is assembled to the frame 3050 as shown in FIG. 28-2, the mesh-like cylinder 3092 extends through the proximal side frame member 3052 and towards the opposite side frame member 3052 of the frame 3050. Also, the distal end of the mesh-like cylinder 3092 extends towards the elbow 3027 attached to the opposite end of the frame 3050 and communicated with the air delivery tube. The distal end may engage with an interior surface of the opposite side frame member, e.g., an interference or friction fit. Similarly, the proximal end of the mesh-like cylinder 3092 may frictionally engage with an interior surface of the end plug 3025. When a nasal prong assembly 3010 (including a base 3020 and a pair of nasal prongs 3030) is attached to the frame 3050 as shown in FIG. 28-3, the mesh-like cylinder 3092 extends through the base 3020 and across the inlets to the nasal prongs 3030.

In use, gas enters through the elbow 3027 and is directed through the mesh-like cylinder 3092 to disperse or dissipate the gas before it enters the nasal prongs 3030 and hence the patient's nasal cavity to reduce irritation. The large surface area of the mesh-like cylinder 3092 prevents any additional impedance to the air delivery circuit.

The above-described arrangement facilitates assembly, removal, and/or replacement of the dispersion cartridge 3090. For example, the end plug 3025 may be easily removed from the frame 3050 to clean and/or replace the mesh-like cylinder 3092 attached thereto. It is noted that the mesh-like cylinder 3092 may be washed and reused, or the mesh-like cylinder 3092 may be made as a disposable item. Also, it should be appreciated that the positions of the end plug 3025 and elbow 3027 may be interchanged, according to preference.

In an alternative embodiment, the mesh-like cylinder 3092 may be attached to the elbow 3027 or opposite side frame member 3052 instead of the end plug 3025. In yet another embodiment, the mesh-like cylinder 3092 may be supported by the side frame members 3052 of the frame 3050, and sandwiched between the elbow 3027 and the end plug 3025 to secure the mesh-like cylinder 3092 in place.

In the illustrated embodiment, the mesh-like cylinder 3092 may be made of a metal or plastic mesh material. However, the mesh-like cylinder 3092 may be made of a fabric or textile material that is gas permeable, e.g., Gortex®. In an alternative embodiment, as shown in FIG. 28-4, a dispersion cartridge 3190 may include a thin-wall plastic or ceramic cylinder 3192 with a plurality of perforated holes 3194 therethrough. For example, the cylinder 3192 may include 1-600 holes or more, e.g., 1-30 rows each having 1-20 holes. In the example shown, the cylinder has 20-25 rows each having 15-20 holes. The holes could be patterned so as to avoid direct jetting into the nasal prongs.

In the illustrated embodiment, the dispersion cartridge 3092 has a cylindrical shape. However, the dispersion cartridge 3092 may have other suitable shapes to fit within the nasal prong assembly, e.g., flat or planar shape.

In another embodiment, a dispersion cartridge may comprise a flat piece of material, e.g., mesh-like material, which is rolled into cylindrical form and then inserted into the frame, elbow, and/or end plug.

The dispersion cartridge 3092 may provide additional uses. For example, the dispersion cartridge 3092 may also be used as a medicine/aromatic dispenser, moisture absorber, and/or humidifying element. For example, medicine may be provided within the dispersion cartridge and adapted to be dispersed as air passes through the dispersion cartridge. In addition, the cartridge may be provided with a filtering function. The filtering can occur as a result of the perforations and/or hole size, or the filtering can be provided by a separate component, such as a filter.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A nasal prong for sealing with a nasal passage of a patient to treat sleep disordered breathing with positively pressurized gas, comprising:
   a head portion structured to seal and/or sealingly communicate with the patient's nasal passage, the head portion including a flexible wall having an exterior surface along an outer side of the head portion and an interior surface along an inner side of the head portion opposite to the outer side, and at least an upper portion of the exterior surface is adapted to contact with the patient's nasal passage; and
   a column or stalk structured to interconnect the head portion with a base, the base defining a plenum for receiving pressurized gas that is delivered to the patient via the column or stalk and the head portion;
   wherein:
   the nasal prong is configured to maintain a seal while the positively pressurized gas is provided to the patient continuously during all stages of respiration including inhalation and exhalation;
   the head portion includes a plurality of discrete protruding elements extending from a prong orifice to a base of the head portion, the prong orifice being configured to be proximal to the patient during treatment, the protruding elements being made from a resiliently deformable material that extends along and protrudes at least partially inwardly from the interior surface of the head portion, the protruding elements being configured and structured to diffuse or create turbulence within an air flow generated by a delivery of the pressurized gas to the patient such that the diffusion or turbulence reduces air jetting effects, the protruding elements being integrated with the interior surface of the flexible wall of the head portion along an entire longitudinal length of the protruding element; and
   at least the upper portion of the exterior surface of the head portion comprises a smooth surface which forms an elliptical or round shape opposite the interior surface, the interior surface opposite the upper portion of the exterior surface including the at least one protruding element protruding internally therefrom.

2. A nasal prong assembly, comprising:
a base; and
a pair of nasal prongs according to claim 1 provided to the base.

3. A nasal prong according to claim 1, wherein the head portion includes a side wall providing the exterior and interior surfaces, the side wall extending from a prong orifice to a rib or base of the head portion, and the at least one protruding portion protrudes at least partially inwardly from the interior surface of the side wall.

4. A nasal prong according to claim 1, wherein the at least one protruding element is adapted to diffuse air flow or create turbulence as pressurized air passes through the head portion in use in order to reduce and/or eliminate air jetting effects.

5. A nasal prong according to claim 1, wherein the nasal prong comprises molded silicone.

6. A nasal prong according to claim 1, wherein the exterior surface includes a concave configuration structured to seal against the patient's nare.

7. A nasal prong according to claim 1, wherein the at least one protruding portion protrudes only along the interior surface of the head portion.

8. A nasal prong according to claim 1, wherein the head portion further comprises an exit orifice structured to have a specific shape which increases the dispersion and turbulence of the airflow as it exits the orifice.

9. A nasal prong according to claim 1, wherein the opening of the head portion closest to the nares of the patient is adapted to cause at least some of the airflow associated with delivery of respiratory therapy to a patient to be directed in a direction other than parallel to the column.

10. A nasal prong according to claim 1, wherein the head portion is constructed with a non-corrugated outer surface.

11. A nasal prong according to claim 1, wherein the head portion substantially maintains its shape during use.

12. A nasal prong according to claim 1, wherein the at least one protruding element is superficial to the interior surface of the head portion.

13. A nasal prong according to claim 1, wherein the protrusions are positioned only on the inner surface.

14. The nasal prong according to claim 1, wherein the head portion includes a conical section with the protruding elements disposed on a curved inner surface of the conical section.

15. A nasal prong according to claim 1, wherein the head portion includes a hood structured to redirect air flow from a direction generally parallel to an axis of the orifice to a second direction angled relative to the axis such that the hood is configured to direct gas in use away from the septum.

16. A nasal prong according to claim 15, wherein the hood includes surface treatment.

17. A nasal prong according to claim 15, wherein the hood is structured to direct gas in use posteriorly relative to the nasal passage.

18. A nasal prong according to claim 15, wherein the hood is provided to an anterior portion of the head portion.

19. A nasal prong according to claim 15, wherein the hood is provided to a medial portion of the head portion.

20. A nasal prong according to claim 15, wherein the hood is integrally formed with the head portion.

21. A nasal prong according to claim 1, wherein the head portion includes a grate structured to diffuse air flow and/or create turbulence.

22. A nasal prong according to claim 21, wherein the grate includes surface treatment.

23. A nasal prong according to claim 21, wherein the grate is provided at a base of the stalk.

24. A nasal prong according to claim 21, wherein the grate is provided at a rim of the head portion.

25. A nasal prong according to claim 21, wherein the grate includes grates that extend generally parallel to a minor axis of an exit orifice.

26. A nasal prong according to claim 21, wherein the grate includes grates that extend generally parallel to a major axis of an exit orifice.

27. A nasal prong according to claim 21, wherein the grate includes grates that are curved or arcuate and define one or more circular or oval openings through the grate.

28. A nasal prong according to claim 1, wherein the head portion includes an exit orifice that is offset from an axis of the head portion.

29. A nasal prong according to claim 28, wherein the exit orifice is shifted posteriorly to direct gas in use posteriorly relative to the nasal passage.

30. A nasal prong according to claim 1, wherein the protruding elements include one or more ribs along the interior surface of the head portion to disperse air flow or create turbulence.

31. A nasal prong according to claim 30, wherein the rib has a helical shape.

32. A nasal prong according to claim 30, wherein the rib has a generally circular, oval, and/or arcuate shape that extends around at least a portion of the interior perimeter of the head portion.

33. A nasal prong according to claim 1, wherein the at least one protruding element adds support and/or rigidity to the head portion.

34. A nasal prong according to claim 1, wherein the at least one protruding element is in direct contact with the interior surface along the entire longitudinal length.

35. A nasal prong according to claim 1, wherein the head portion includes a side wall providing the exterior and interior surfaces, the side wall extending from a prong orifice to a rib or base of the head portion, and the at least one protruding portion extends along at least an intermediate portion of the side wall between the prong orifice and the rib or base.

36. A nasal prong for sealing with a nasal passage of a patient during use of a respiratory therapy device, comprising:
a head portion structured to seal and/or sealingly communicate with the patient's nasal passage; and
a column or stalk structured to interconnect the head portion with a base, the base defining a plenum for receiving pressurized gas that is delivered to the patient via the column or stalk and the head portion;
wherein
the upper surface of the head portion is adapted to contact with the patient's nasal passage;
the head portion includes a grate made from a resiliently deformable material, the grate including a plurality of grates oriented to extend across a longitudinal axis of a prong exit orifice, the grate being structured to create turbulence within an air flow generated by a delivery of pressurized gas to the patient; and the base, the column or stalk, the grate, and the head portion together define a flow path through which pressurized gas must pass before entering the nasal passage of the patient.

37. A nasal prong according to claim 36, wherein the resiliently deformable material includes any one from the group consisting of: silicone, waterproof/breathable fabric and a textile membrane.

38. A nasal prong according to claim 36, wherein the prong exit orifice includes a generally oval shape.

39. A nasal prong according to claim 38, wherein the grates are oriented to extend generally parallel to a minor axis of the prong exit orifice.

40. A nasal prong according to claim 38, wherein the grates are oriented to extend generally parallel to a major axis of the prong exit orifice.

41. The nasal prong according to claim 36, wherein the grate is contained within the head, column or stalk, or a transition area between the head and column or stalk.

42. The nasal prong according to claim 36, wherein pressurized gas must pass through the grate before entering the head portion.

43. The nasal prong according to claim 42, wherein the grate is located between the column and the head portion.

44. The nasal prong according to claim 42, wherein the grate is located between the column and the head portion.

45. The nasal prong according to claim 36, wherein pressurized gas must pass through the base followed by the column followed by the grate and then through a least a portion the head portion and then through an orifice of the nasal prong to the patient.

46. The nasal spray according to claim 45, wherein the grate is located within the head portion.

47. A nasal prong for sealing with a nasal passage of a patient, comprising:
  a head portion structured to seal and/or sealingly communicate with the patient's nasal passage; and
  a column or stalk structured to interconnect the head portion with a base, the base defining a plenum for receiving pressurized gas that is delivered to the patient via the column or stalk and the head portion;
wherein
  at least a portion of an outer surface of the head portion is adapted to contact and seal along the patient's nare;
  the head portion includes a grate formed in one piece with the head portion, the grate including a plurality of grates oriented to extend across a longitudinal axis of a prong exit orifice, the grate being structured to create turbulence within an air flow generated by delivery of pressurized gas to the patient; and
  the base, the column or stalk, the grate, and the head portion together define a flow path through which pressurized gas must pass in use before entering the nasal passage of the patient.

48. A nasal prong according to claim 47, wherein the grate is formed as a unitary piece along with the nasal head portion.

49. The nasal prong according to claim 47, wherein the grate is contained within the head, column or stalk, or a transition area between the head and column or stalk.

* * * * *